United States Patent
Treat et al.

(10) Patent No.: US 7,164,968 B2
(45) Date of Patent: Jan. 16, 2007

(54) ROBOTIC SCRUB NURSE

(75) Inventors: Michael R. Treat, New York, NY (US); Martin T. Lichtman, Stanford, CA (US); David M. Brady, Astoria, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 333 days.

(21) Appl. No.: 10/408,799

(22) Filed: Apr. 7, 2003

(65) Prior Publication Data

US 2003/0216836 A1 Nov. 20, 2003

Related U.S. Application Data

(60) Provisional application No. 60/370,523, filed on Apr. 5, 2002, provisional application No. 60/370,924, filed on Apr. 8, 2002.

(51) Int. Cl.
*G06F 19/00* (2006.01)
(52) U.S. Cl. .................. 700/245; 700/246; 700/247; 700/248; 700/249; 700/258; 700/259; 700/260; 600/102; 600/130; 606/205; 606/130; 606/139; 318/568.11; 901/1; 901/2; 901/9
(58) Field of Classification Search ........ 700/245–249, 700/258–264; 600/102, 130; 606/205, 130, 606/139; 318/568.11; 901/1–2, 9; 414/1–2
See application file for complete search history.

(56) References Cited

U.S. PATENT DOCUMENTS 4,837,734 A * 6/1989 Ichikawa et al. ........... 700/249
5,187,796 A 2/1993 Wang et al.
5,297,149 A * 3/1994 Kazato ........................ 714/24

(Continued)

FOREIGN PATENT DOCUMENTS

EP 0 663 271 A2 1/1995

(Continued)

OTHER PUBLICATIONS

Davies, Robotics in minimilly invasive surgery, 1995, Internet, p. 1-2.*

(Continued)

*Primary Examiner*—Thomas Black
*Assistant Examiner*—McDieunel Marc
(74) *Attorney, Agent, or Firm*—Wolf, Block, Schorr & Solis-Cohen LLP; William H. Dippert

(57) ABSTRACT

A robotic system, and corresponding method, performs the function of a human scrub technician in an operating room. A device, and associated method for using the device, performs one, or more, of the following functions: instrument identification, instrument localization, instrument handling, interaction with a human, and integration of functions through a cognitive system. A method for movement of the device comprises the steps of modeling the arm of the robot to create a model comprising elements of finite mass joined by junctions, using an algorithm to calculate results of the effect of applying force to the elements of the model, using attractive, repulsive and postural forces in the algorithm, and using the results of the model to direct motion of the device.

34 Claims, 11 Drawing Sheets

Top view of the Robotic Scrub Tech layout

U.S. PATENT DOCUMENTS

| | | | |
|---|---|---|---|
| 5,515,478 A | 5/1996 | Wang | |
| 5,524,180 A | 6/1996 | Wang et al. | |
| 5,553,198 A | 9/1996 | Wang et al. | |
| 5,645,520 A | 7/1997 | Nakamura et al. | |
| 5,649,956 A * | 7/1997 | Jensen et al. | 606/205 |
| 5,657,429 A | 8/1997 | Wang et al. | |
| 5,754,741 A | 5/1998 | Wang et al. | |
| 5,762,458 A * | 6/1998 | Wang et al. | 414/1 |
| 5,815,640 A | 9/1998 | Wang et al. | |
| 5,841,950 A | 11/1998 | Wang et al. | |
| 5,847,359 A * | 12/1998 | Sugahara et al. | 219/121.72 |
| 5,855,583 A | 1/1999 | Wang et al. | |
| 5,878,193 A | 3/1999 | Wang et al. | |
| 5,907,664 A | 5/1999 | Wang et al. | |
| 5,911,036 A | 6/1999 | Wright et al. | |
| 5,971,976 A | 10/1999 | Wang et al. | |
| 5,986,651 A * | 11/1999 | Reber et al. | 715/738 |
| 6,001,108 A | 12/1999 | Wang et al. | |
| 6,007,550 A | 12/1999 | Wang et al. | |
| 6,063,095 A | 5/2000 | Wang et al. | |
| 6,102,850 A | 8/2000 | Wang et al. | |
| 6,132,441 A | 10/2000 | Grace | |
| 6,202,004 B1 | 3/2001 | Valerino, Sr. | |
| 6,244,809 B1 | 6/2001 | Wang et al. | |
| 6,304,050 B1 | 10/2001 | Skaar et al. | |
| 6,309,397 B1 | 10/2001 | Julian et al. | |
| 6,436,107 B1 * | 8/2002 | Wang et al. | 606/139 |
| 6,463,361 B1 | 10/2002 | Wang et al. | |
| 6,496,099 B1 | 12/2002 | Wang et al. | |
| 6,699,177 B1 * | 3/2004 | Laby et al. | 600/102 |
| 2002/0133174 A1 | 9/2002 | Charles et al. | |
| 2003/0033024 A1 | 2/2003 | Sunaoshi | |
| 2003/0045888 A1 | 3/2003 | Brock et al. | |
| 2003/0050733 A1 | 3/2003 | Wang et al. | |

FOREIGN PATENT DOCUMENTS

| | | |
|---|---|---|
| EP | 0 667 124 A1 | 1/1995 |
| EP | 0 875 207 A2 | 4/1998 |
| WO | WO 96/30718 | 10/1996 |
| WO | WO 00/21071 | 4/2000 |
| WO | WO 00/30548 | 6/2000 |

OTHER PUBLICATIONS

Willimas et al., Surgery benefits from defense technology: Computer assisted minimally invasive surgery (CAMIS), 1994, IEEE, p. 3-6.*

Mack, Minimally invasive and robotic surgery, 2001, Internet, pp. 568-572.*

Chitwood, jr., Development and implementation of surgical robot program, 2002, Internet, p. 1-52.*

Bukchin et al., teaches learning in tele-operations, 2001, pg. 1-8.*

* cited by examiner

OVERALL VIEW OF THE ROBOTIC SCRUB TECH IN ACTION, SHOWING
SPATIAL AND FUNCTIONAL RELATIONSHIP TO SURGEON AND PATIENT

Detail of the Shoulder of the Robot Scrub Tech, showing the "twist" degree of freedom.

Also showing use of carbon fiber rods to form a very light and stiff structure

In this picture, the arm is pointing straight up, in order to show the twist servo arrangement.

FIG. 4(a)

Detail of the ElectroMagnetic Gripper, showing the servo motor and the compliant mount

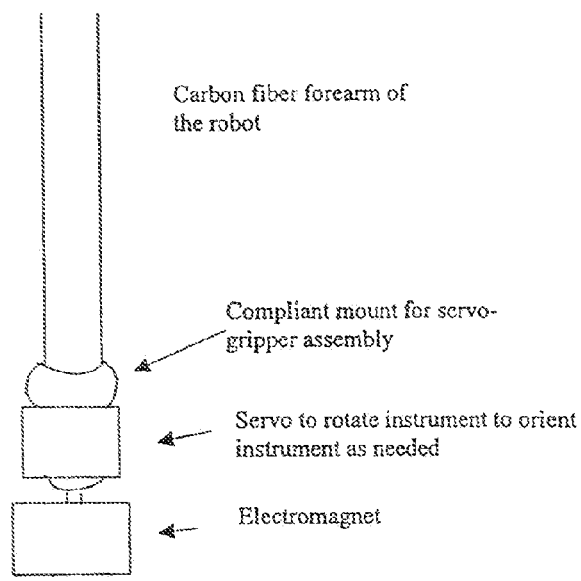

Carbon fiber forearm of the robot

Compliant mount for servo-gripper assembly

Servo to rotate instrument to orient instrument as needed

Electromagnet

FIG. 4(b)

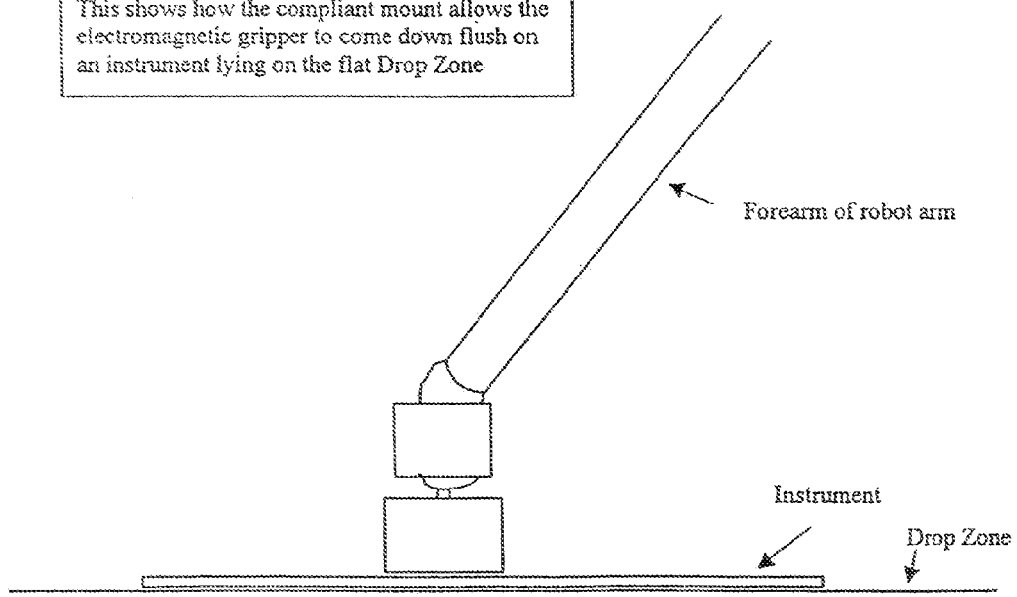

This shows how the compliant mount allows the electromagnetic gripper to come down flush on an instrument lying on the flat Drop Zone Forearm of robot arm Instrument Drop Zone INITIAL CONDITIONS for Infinitesimal Spring Method STEP 1 Application of a Force STEP 2 Movement of Rod1 and stretching of Spring1 in response to the force. Rod2 has not had a chance to move yet.

STEP 3 Movement of Rod2 has just occurred and new temporary equilibrium reached.

Obtaining hinge motion using infinitesimal spring constructs

Fixed Points a and a' to constrain
crossmember b-b' attached to Hinged rod

Example of a two-element system with two hinges.

HingedBody rotating about its hinge-pin at the hinge-point "a".

ROBOTIC SCRUB NURSE

CROSS-REFERENCE TO RELATED APPLICATION

This application corresponds to co-pending U.S. provisional patent applications Ser. No. 60/370,523, filed Apr. 5, 2002, and Ser. No. 60/370,924, filed Apr. 8, 2002, both of which applications are incorporated herewith by reference.

FIELD OF THE INVENTION

The present invention generally relates to an automated, autonomous device, and a method for its operation. More specifically, the present invention relates to a robotic scrub tech system, which is an automated, autonomous device that replaces a scrub nurse or technician in an operating room context.

BACKGROUND OF THE INVENTION

In a surgical operating room, the scrub nurse or scrub technician manages an assortment of surgical instruments. When not in use, these instruments are placed on a tray, denoted a Mayo stand. When a surgeon verbally requests one of the instruments, the technician takes the instrument off the Mayo stand and hands it to the surgeon. When finished with the instrument, the surgeon lays the instrument down in an area that can be referred to as the "drop zone." At this point, the technician retrieves the instrument from the drop zone and returns it to the Mayo stand, so that it is ready to be used again.

It is desired that the tasks of the technician be performed by a robotic device, so that the tasks are performed with greater speed and economy.

The present invention describes how the tasks of the scrub technician can be automated using the technologies of speech recognition, machine vision, robotic arm path planning, and artificial intelligence. The present invention discloses prototypes capable of performing the essential job functions of a human scrub technician. One prototype comprises a five (5) degree of freedom robotic arm with a electromagnetic gripper, a digital camera which surveys the instrument drop zone, and means to provide voice recognition and voice synthesis capabilities. Furthermore, in addition to these physical and sensory capabilities, the prototype can have a higher-level cognitive layer integrating these basic functions.

Devices within the scope of the present invention perform traditional scrub tech functions faster and more accurately than do the human scrub technicians. Further advantages of the devices may include the following: The device can be more adaptable to a variety of surgeons. For example, surgeons have considerable individual preferences and variations in terms of instruments and patterns of instrument usage. A human scrub technician will have difficulty remembering preferences and variations of even a single surgeon, especially when that technician is not assigned to that surgeon a regular basis. On the other hand, a robotic device of the present invention will be able to adapt to the individual surgeon's preferences, and, remember these preferences from case to case. This would provide the surgeon with the benefit of having an assistant who is readily adapted to the surgeon's individual style. Separately, devices of the present invention will be more suitable to inventory functions. A robotic device of the present invention provides a high level of security and of accuracy in terms of counting and tracking the instruments used in a case. With a human technician, keeping accurate count and accounting for each and every instrument used in a case continues to be a source of some difficulty and concern for the hospital operating room staff. Also, since the robotic device is always available in the operating room, it may eliminate or reduce the need for overtime staffing, which may not always be readily available as desired and which in any event is an extra expense for the hospital.

SUMMARY OF THE INVENTION

The present invention is generally directed to a device, and associated method for using the device, which performs the functions of a human scrub technician in the operating room.

The present invention specifically is directed to a device, and associated method for using the device, which performs one, or more, of the following functions: instrument identification, instrument localization, instrument handling, interaction with a human (such as surgeon), and integration of functions through a cognitive system. An embodiment of the device is depicted in FIGS. 1–4.

An embodiment of the present invention is a method for performing the function of a human scrub technician, which includes steps selected from identifying an instrument, using machine vision, by size, shape, color, or other distinctive feature, either in response to a human command or via artificial intelligence;

identifying the location of an instrument, with or without human assistance;

handling an instrument, such that the instrument can be picked up, conveyed, and released;

interacting with a human, such as a surgeon, to apprehend the intentions of the human, by means of sound (e.g., verbal requests) or by means of vision (e.g., visual recognition of gestures) or touch (e.g., by means of tactile inputs); and integrating the functions.

An embodiment of the invention is a method comprising one, or more, of the following steps:

initiating a search for the instrument;

identifying the instrument by a characteristic feature by machine vision;

determining the location of the instrument;

picking up the instrument;

moving the instrument from a first location to a second location; and releasing the instrument, wherein each step is performed by the robotic device.

An embodiment of the invention is a method for moving an arm of a robot comprising the steps of modeling the arm of the robot to create a model comprising elements of finite mass joined by junctions; using a physics based algorithm to determine results of the effect of applying force to the elements of the model; and using the results to define a path for the arm of the robot.

BRIEF DESCRIPTION OF THE DRAWINGS

FIGS. 4(a) and 4(b) represent details of an electromagnetic gripper of an embodiment of the invention such as shown in FIGS. 1 and 2, showing the servo motor and the compliant mount;

DETAILED DESCRIPTION OF THE INVENTION

Figure 1:
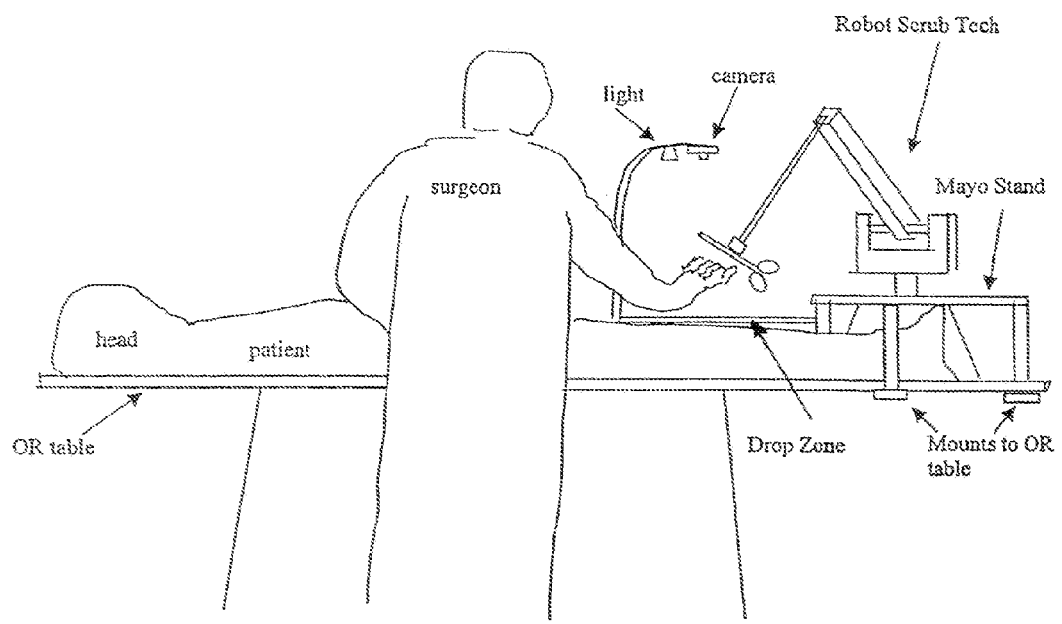
FIG. 1 is an overall view of an embodiment of the invention, showing spatial and functional relationship of surgeon and patient.

Generally, the present invention represents a novel approach to an automated, autonomous system to perform the functions of a human scrub technician. The present invention is directed to a device and method which manifest the functions of instrument identification, instrument localization, instrument handling, interaction with a surgeon, and integration employing a cognitive system. The present invention is also directed to a method of picking up an object by means of calculating the center of mass in two dimensions and picking up the device at its center of mass in two dimensions. The present invention is further directed to a physics based model of a robot arm, and a method of movement of said arm based upon said model.

In one embodiment of the invention, a robotic system employs (1) speech recognition to respond to a spoken request for a particular surgical instrument, (2) a machine vision system that uses size of the surgical instrument or color of the surgical instrument to distinguish among four instruments to identify the particular surgical instrument, (3) a center of mass algorithm to pick up the surgical instrument at an optimum position, and (4) a electromagnetic gripper to pick up the surgical instrument, to move the surgical instrument, and to release the surgical instrument in proper position. The system then re-initializes to await the next request.

DETAILED FUNCTIONAL DESCRIPTION OF DEVICE

1. Instrument Identification:

This refers to the ability of the RST [Robot Scrub Technician, an embodiment of the present invention] to become aware of what type of instrument it is dealing with, without any input or hints from a human operator. For example, when the RST retrieves an instrument which the surgeon is no longer using, the RST needs to be able to identify what that instrument actually is, so that it can return that instrument to its proper place on the instrument tray and be ready to hand it out again when requested by name. Since there are many types of instruments that could be used at the same time, the robot needs to be able to determine on its own what instrument has been put down by the surgeon. For example, a surgeon might sequentially request a retractor, then a hemostat, and then a scissors in order to perform a certain step of an operation. After this step is finished, it is not definitely predictable which of these three instruments would be returned first. Although the robot could (and should) maintain probability tables as to the likelihood of which instrument would be returned first, for robust and error free operation, the RST is able to identify the instruments by direct observation of some sort of sensory data. An embodiment of the RST would work with standard surgical instruments already in use in operating rooms.

Machine Vision for Instrument Identification

A preferred embodiment of the identification function could be a digital camera feeding image data to software or hardware implementing various known machine vision and image processing techniques. Appropriate techniques can use as an image data sources either gray-scale or color vision cameras. To distinguish between specific instruments such as a hemostat versus a scissors, it is possible to use the area or size of the two dimensional outline of the instrument. Other features which lend themselves to the correct identification of instruments are the aspect ratio of the instrument and various moments of gravity, calculated from the two dimensional projection of the instruments. Additional features are the detection of certain angles or curves that would be unique to one type of instrument. For example, the very acute angle formed by the pointed tips of certain types of scissors can be used as a identification marker. Also, template matching of the outline or silhouette of the instrument is a useful technique to distinguish one instrument from another. In one embodiment of the invention the two dimensional projection of the instrument and/or color of the instrument is used.

Use of Multiple Instrument Identification Techniques

It is preferred to use a battery of instrument identification techniques in order to improve the reliability of the identification process. The robot's software keeps track of the accuracy rate of the various techniques used, and if certain ones were doing better, those ones could be given greater weight in the recognition process.

Use of a Stored Data Base of Instrument Recognition Characteristics

In one embodiment of the invention, the robot maintains in computer memory a database of the observed values for the various characteristics that it uses to identify various instruments. For example, depending on slight variations in ambient lighting and also in the surface optical characteristics of instruments, there might well be some variation in the perceived (by the robot's machine vision system) of the measured size of an instrument. It is useful for the robot to maintain a table or histogram of the number of times a particular measurement of size was associated with a particular instrument. In this way, it can employ statistical techniques to determine the probability that a measured size of instrument could be validly associated with that instrument. It is also possible and useful, given such a data base of several characteristics, to perform multivariate statistical analysis to help multivariate statistical analysis to help the robot reach a more reliable decision as to the identity of the observed instrument.

Drop Zone

The observation and calculation of these various visually determined features of instruments is greatly facilitated by the incorporation of a specially designed area on the operating table known as a "drop zone." The drop zone facilitates the correct identification of surgical instruments by simplifying the task of the machine vision recognition by constraining the presentation (i.e. the spatial orientation and applied illumination) of the instruments to the machine vision recognition system. In a preferred embodiment the instruments are constrained to be presented in essentially a two dimensional way. This approach would work for most, if not all, simple surgical instruments such as hemostats, scissors, retractors, since when laid down on a flat surface, these instruments all must lie down flat. The importance of this constraining of the visual recognition task cannot be overstated. This preferred embodiment allows the machine vision routines to work quite robustly using modest computing resources.

A preferred embodiment of the drop zone would be a flat rectangular area, approximately 24 inches by 18 inches, located over a patient's lower body and thighs, in the case of an abdominal operation. This drop zone, in location and extent, is roughly the same as the area of the dropped patient's body upon which surgeon's customarily put down an instrument when finished with it, so that the scrub nurse can pick it up and return it to the instrument tray. As part of the drop zone concept, the digital imaging camera is constrained to view this area in a direct, orthogonal way, with controlled ambient lighting. In one embodiment, the digital camera is mounted on a boom which positions it directly over the drop zone. Conceptually the drop zone provides a more structured version of the area which has evolved by common usage as a dropping off place for instruments with which the surgeon is finished so that the scrub nurse can pick them up and return them to the instrument tray. In addition to having regular and certain dimensions, the drop zone is flat, and colored and textured in such as way as to enhance the ability of the machine vision camera to visualize instruments with consistent, even, and glare free lighting. Special lighting arrangements to improve the accuracy of the machine vision system could be incorporated into the drop zone either by booms or pedestals to hold the lighting fixtures or even by lighting incorporated to provide backlighting through a semitransparent surface of the drop zone.

2. Instrument Localization:

Instrument Localization refers to the ability of the RST to determine without human assistance precisely where an instrument is on the drop zone or instrument tray, in order to be able to direct its manipulator arm to that instrument, and to position its gripper over the correct place on the instrument to effect stable and balanced pick-up of the instrument.

Drop Zone as an Aid to Localization

The drop zone is a feature of the Instrument Localization function of the RST. In a preferred embodiment, which has been implemented by the inventors, the drop zone is physically integrated and registered into the overall physical construction of the robot so that it is possible to compute the location of the instrument relative to the coordinate system of the robot's manipulator arm, given the coordinates of the instrument relative to the drop zone. Alternatively, the drop zone can be designed so that it is removable but attachable in a certain constrained way, to the rest of the framework of the robot.

Special Instrument Tray

The instrument tray is a tray adjacent to the scrub nurse upon which are located the instruments which are going to be immediately used by the surgeon. Typically, this tray measures about 18 by 12 inches and can hold approximately 12 instruments. It is sometimes referred to as the "Mayo stand". The robotic scrub tech's instrument tray would be specially configured to provide for the orderly arrangement of the instruments used in a case. This configuration could be embodied by the use of slots, grooves or specially bordered areas on the tray to accommodate instruments individually. These slots could incorporate sensors, such as pressure pad switches or metallic proximity sensors, which could inform the robot that an instrument was occupying one of the slots.

The special instrument tray can also incorporate bar-code type scanning capability to further allow the robot to be aware of exactly what instruments were residing in the slots of the tray.

This information about the number and type of instruments used could also be saved by the robot and passed onto the inventory control computer of the operating room. This information could also be used to track usage of various items at the level of the individual surgeon.

Machine Vision for Instrument Localization

A preferred embodiment for the Instrument Localization function is a digital camera feeding image data to software or hardware based algorithms which could compute the location of the center of gravity of the instrument, in the coordinate system of the camera, and then to relate that point to the coordinate system of the robotic arm, using appropriate coordinate transformation mathematics such as matrices which perform coordinate translation, rotation and other transforms. This embodiment has been implemented by the inventors. Such transformation matrices could also be used to calibrate the motions of the robot's arm, so that inaccuracies in the physical construction of the arm which would cause to the arm to be off-target, could be adjusted for by means of self-calibration of the motion of the arm under the observation of the robot's own visual system.

Other Sensing Techniques for Instrument Localization

Other embodiments for the Instrument Localization function are done using sensors for ferromagnetic material such as Hall effect sensors, proximity sensors based on changes in the capacitance of a tuned RF circuit ("metal detector circuits"), optical or ultrasonic sensors which rely on triangulation techniques to pinpoint the location of a body equipped with an appropriate ultrasonic or optical emitter, magnetic field distortion based sensors, sensing based on reflection of pulses of laser light or ultrasonic emissions, and others.

3. Instrument Pick-Up Conveyance, Positioning, Orientation:

Another cardinal function of the RST is the ability to physically pick-up, convey from point to point, position with regard to the surgeon and other reference points, and orient the direction of the instruments so that it can be placed in the correct orientation relative to other instruments on the instrument tray. These individual functions are collectively referred to as instrument handling.

Designated Pickup Point at Center of Area of the Instrument

A feature of a preferred embodiment of the Instrument Handling function of the RST is the use of a designated pick-up point on each instrument. This pick-up point typically would be the center of gravity (center of area of the two dimensional projection of the instrument on the drop zone. That is, for flat instruments which are lying flat on the drop zone the center of area will coincide with the center of gravity or center of mass). The use of the center of gravity as single designated pick-up point simplifies the targeting requirements and the dexterity requirements of the gripper. This embodiment has been implemented by the inventors.

This pickup point in a preferred embodiment can be marked with a distinctive optical marker than can be readily located by whatever instrument visualization capability the robot is to employ.

ElectroMagnetic Gripper

Because of the use of the center of area (which coincides with the center of mass for flat instruments of uniform density) of the instrument as the designated pick-up point, it is possible to use a simple electromagnetic gripper to stably convey a surgical instrument as illustrated. An electromagnetic gripper, as opposed to a permanent magnet gripper, is a preferred embodiment since the electromagnet can be switched off at the appropriate time to permit release of the instrument by the robot into the surgeon's hand. This embodiment has been implemented by the inventors.

Other single-point type grippers can also be used, such as grippers based on suction or vacuum effects. Without use of the center of mass concept, a typical surgical instrument which is being picked up by a simple electromagnetic gripper would tend to dangle off the magnet in somewhat unpredictable ways. By using the center of mass, the magnetic gripper can hold that instrument steadily and also be able to effect rotational orientation of the instrument in a plane parallel to the drop zone and instrument tray planes.

Orientation of the Instrument

Determination of the orientation of the instrument is simplified by our constraining the problem to be in two dimensions. Orientation of the instrument is accomplished by the determination of the angle at which the instrument is initially oriented, relative to a coordinate frame based on the robot's gripper. Observation of this angle is followed by computation of the amount of rotation needed to put the instrument into the desired orientation to lie compactly on the instrument tray, after the arm has moved (and thereby re-oriented the instrument) the instrument back to the instrument tray. These calculations are accomplished by a straightforward application of transformation matrices for the desired rotations. This embodiment has been implemented by the inventors.

This orientation determination depends only on rotational transformations between the various coordinate systems, and not on any translational transformation that might arise from the conveyance of the instrument from the drop zone to the instrument tray. For example, an instrument is retrieved from the drop zone at an orientation of 45 degrees clockwise relative to a coordinate system that is attached to the robot's gripper. In this example, the robot's arm was oriented at an angle 45 degrees counterclockwise relative to a coordinate system attached to the frame of reference of the camera. Taking this example a step further, assume that the robot's arm will be oriented at 60 degrees clockwise when the arm is over the position of the instrument tray that the instrument should be returned to. In order to have the instrument lined up correctly on the instrument tray, it will be necessary to rotate it by a certain number of degrees relative to the gripper coordinate system. In general, it is not obvious from simple inspection of the situation what that re-orientation angle should be but this reorientation angle can calculated in a straightforward fashion using rotation matrix mathematics to keep tract of the conversions from one coordinate system to the next.

In a preferred embodiment, the robot distal arm is equipped with a servomechanism which is capable of rotating the orientation of the instrument. This embodiment has been implemented by the inventors. In this preferred embodiment, the robot's machine vision system observes the initial orientation of the instrument when it is first picked up. Computations are done, using rotation matrix mathematics, to determine how the instrument should be re-oriented so that it ends up in the correct orientation relative to the instrument tray after the robot's arm has moved around in an arc from pickup point to appropriate location on the instrument tray.

Constraining of the Positioning Problem to Two Dimensions

Constraining the location of the instruments to approximately two dimensions has already been mentioned in terms of the Instrument Identification function. The concept of constraining the location to approximately two dimensions is important to one embodiment of the successful, robust and fairly inexpensive implementation of the Instrument Handling function of the robot, since it is much more difficult to do so in three dimensions. Two dimensional constraint is accomplished by the planar nature of the drop zone and the instrument tray, and also, importantly, by the fact that the drop zone and the instrument tray are themselves co-planar. Therefore, when retrieving an instrument from the drop zone and placing it on the instrument tray, the robot only needs to be concerned with angular orientation of the instrument in a plane parallel to the drop zone and instrument tray planes, and with the translational aspects of the motion from drop zone to instrument tray. The robot does not have to deal with the potentially much more complicated problem of full six degree of freedom orientation of the instrument in three dimensional space.

Physics-Based Simulation for Controlling the Path of the Robot's Arm:

A preferred embodiment is the use of results from a physics-based simulation for the motion control system software. This embodiment has been implemented by the inventors.

This software employs a physics-based simulation or modeling of the motion of the arm in order to provide angular and positional data to specify the motion of the servo motors actuating the joints of the robot's arm so as to achieve a desired path of the robotic arm through space and toward the desired goal. The simulation or model incorporates the laws of Newtonian classical mechanics. It should be appreciated that the coordination of motion for a complex robotic arm is not trivial, since the motion, velocity and acceleration of each joint or degree of freedom must be individually specified. One cannot just tell the robot arm to "go from here to there", but one must compute or specify every point along the path from "here" to "there". This means that each joint must be told by the software how much to move and how fast to move. Additionally, one must decide on what particular path the robot arm is going to follow in going from "here" to "there". One can readily imagine that if one were to pick up a pencil from a desktop, that there are many ways in which one might move one's arm to grasp that pencil. Some of these motions look more "natural" than others or look "graceful", but it is not obvious or trivial to say how the brain actually decides on the actual path. Specification of that path clearly requires some sort of intelligent algorithm to pick the path. In general, this is a difficult though not insoluble problem using conventional approaches to directing the motion of a robotic arm with many degrees of freedom. The software according to the invention greatly facilitates the calculation of a natural appearing, energy efficient, and aesthetically pleasing motion for the robot arm, while using very modest computing resources.

Essentially, the software path-planning algorithm is based on the conception of modeling the robotic arm with a series of rods or segments possessing a three dimensional extent with mass and moments of inertia. The length, mass and other mechanical characteristics (e.g., center of mass) of the computer model will match those of the actual robot upperarm and forearm. These rods can be connected, in the model, by infinitesimally small springs, whose force constants can be adjusted to make the arm compliant in different ways as desired. The rods can also be connected by means of hinges, pivots or sliders which constrain (in the software model) the relative allowed motions of the rods. Additionally, an artificial "anti-gravity" field can be turned on by the software in order to provide the robot with an erect posture. Additionally, the rods are provided with both linear and rotational dampers that can exert frictional forces on the motion of the rods-springs system. These adjustable frictional and damping forces are useful in altering the nature and speed of the robot's movements. The simulation is run by applying an imaginary attractive force to the end or to other parts of the arm and then allowing the mass, inertia, spring forces, hinge or pivot constraints, gravity force and damping forces to determine the motion of the arm. Although the arm's motion is a complex blend of shoulder and elbow position and velocities and accelerations, this unique software allows the very efficient calculation, from simple physical principles, of the path of the robot arm, including all of its joints with all of their degrees of freedom. The angular and positional coordinates, velocities and accelerations of the component of the arm can be retrieved from the arm model as the simulation progresses and used to specify the actual angular rotations of the servo motors which are attached to the joints and other articulation points of the physical robot. In essence, a mathematical model of the robot arm is being employed, and the model is endowed with realistic physical properties such as mass, moments of inertia, friction and springiness. The complex motion of the arm is a result of the interaction of this physical based with the applied forces. This method of planning the robot arm's path is different from the more traditional approach of computing the inverse kinematics of the arm according to an arbitrary algorithm that determines how to move each joint of the robots arm. The system described herein provides a physics-based motion control system that yields remarkably smooth and life-like motions with a rather small amount of computing resources. This software also provides for the means to avoid obstacles to the robot's path.

Modeling of Joints and other Articulations

Several types of software constructions may be used to model the joints or articulations between the segments or rods that comprises the software model of the actual robot's arm.

Connected Spring Model

Overview of Connected Spring Model

In one software embodiment, which has been previously implemented in one version of the RST, infinitesimal springs are located where there are to be joints between the rods. Thus, the configuration in the model of the connected rods and the interconnecting springs is the same as that of the actual robot arm. It is important to this modeling system that the springs be of infinitesimal extent and also that the springs have rather high force constants (i.e., that the springs be rather stiff). The purpose of the springs is to provide a coupling of a force applied to one rod to the entire configuration of rods. Consider a simple system involving two rods connected by an infinitesimal spring. Consider how the configuration of that system evolves over a series of discrete time steps in response to an applied force. In the first time step, a force is applied to one of the rods. The force will first of all result in motion of the rod to which the force is directly applied. The position that the first rod assumes after the force is applied is known from the laws of Newtonian mechanics as applied to rigid body possessing mass, center of mass and moments of inertia. The motion of this rod will then result in a stretching of the spring, according to Hooke's law, which in the next time step will apply a force to the next connected rod. Just as was done for the first rod, the motion of the connected rod resulting from the force applied by the spring is calculated using Newtonian mechanics. This process is repeated iteratively, moving each rod incrementally at each time step of the simulation. The spring is the means by which force resulting from motion of the first rod is applied to update the position of the connected rod. These calculations are done by simple and fast numerical integration methods and thus, the model is computationally efficient and runs well with modest computing resources. Even complex real systems are simple to construct using this modeling method. A crucial advantage of using infinitesimal springs that are very stiff is that the model will not be stretched out of shape as the force is applied. In fact, the spring constant (degree of stiffness) of the spring can be chosen sufficiently high that the degree of elongation of the modeled joints is of a similar order of magnitude to the natural mechanical play of real joints.

The use of intrinsic damping forces is needed in the model to prevent high accelerations from causing the kinematics calculations to go out bounds. The potential for numerical instability of the stiff infinitesimal spring approach is something that must be controlled.

A segment or rod which is connected by a single infinitesimal spring to an imaginary immovable surface will be able to move as though the rod where attached by a ball and socket joint so the free end of the rod can describe points on the surface of a hemisphere centered at the attachment point to the spring. However, by placing two infinitesimal springs along the axis of rotation of a modeled joint, that joint can be constrained to one degree of freedom, so that the end of the rod will describe only an arc of a circle. Additional springs may be employed to produce other constrained motions.

Detailed Discussion of Physics Based Simulation Using Infinitesimal Springs to Join Rods Consider a simple system, composed of two rods connected by a spring, as shown, for example, in FIGS. 5(a) to 5(d).

As in other embodiments of our Physics Based Simulation, the rods are assigned values of physical properties including mass, length, width, height and distribution of mass from which other physical properties such as center of mass and moments of inertia about chosen axes of rotation can be derived in a straightforward fashion. The free end of Rod1 is denoted by point "c" and the other end of this rod is connected to the "b" point of a spring. The "a" point of Spring1 is connected to one end of Rod2 and the other end of Rod2 is connected to Spring2's "b" point. The "a" point of Spring2 is attached to a Fixed Point, which is a specially point that mathematically is constrained to be stationary in terms of its spatial location. For clarity, we also show the center of gravity point "cg" for each rod.

Now consider the following Steps in a simulation of motion of this system in response to an applied force F. In this example, this force is designated to be constant in magnitude and direction but it could in a more general case have a varying magnitude and direction.

STEP 1

Apply a Force F to point "c". In responses to this Force F, Rod1 will begin to move. (see FIG. 5(b)). Using Euler's method or any other similar method of numerical integration of the equation of motion, we can compute the incremental change in the position of Rod1. A general way of handling these equations of motion in three dimensions is to calculate the angular motion in the coordinate frame or the rod, since the moment of inertia and its inverse will be invariant in this frame, and to separately calculate the translational motion of the center of mass of the rod in World coordinates. In the three dimensional treatment a quaternion is used to keep tract of the angular motion of the rods. This mathematical treatment is essentially the same as that described in the other sections of this application dealing with the Hinged-Body implementation of the simulation. As with all embodiments that we have discussed for our physics based simulation, it is important to realize that this is an incrementally moving simulation occurring in finite time-steps.

STEP 2

Figure 5A:
FIGS. 5(a) and 5(d) illustrate the infinitesimal spring method, namely, the initial conditions (5(a)); Step 1: the application of a force (5(b)); Step 2: movement of Rod1 and stretching of Spring 1 in response to a force (5(c)); and Step 3: movement of Rod 2 (5(d))
Figure 5B:
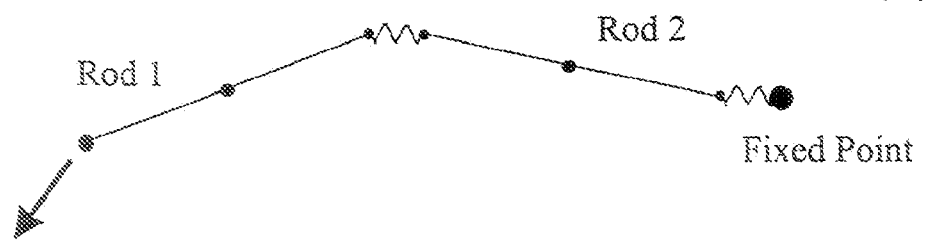
Figure 5C:
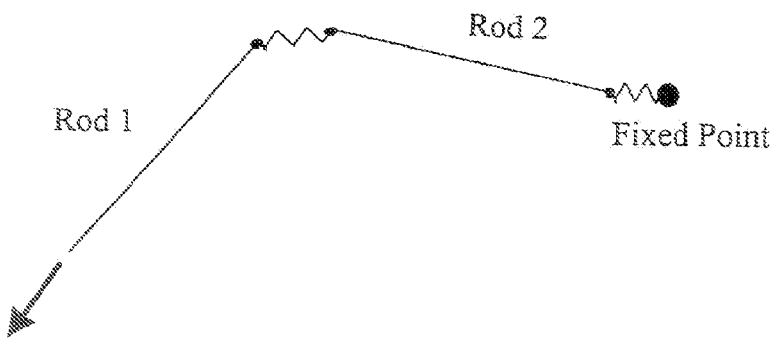

In this step, the key and distinguishing features of the infinitesimal spring method are described, namely, that we use the mathematical construct of a spring as a means of conveying the applied force F from rod1 to rod2 (see FIG. 5(c)). In the HingedBody implementation, we use the mathematical construct of filtering out the components of applied force that the hinge was allowed to respond to. In the spring embodiment, what is done is as follows:

In response to applied Force F, after this time-step, Rod1 has moved downward somewhat and has also undergone some rotation about is center of gravity. The exact amount and direction of that motion will be determined by the physics of the response Rod2 to the applied force. At this time, however, rod2 has not yet moved. The motion of rod1 causes a change in the position of the "b" point of Spring1, which causes a stretching and rotation of this spring. The spring is attached by its "b" and "a" points to rod1 and rod2 and the spatial location of these points is determined by the rods. Now, before F was applied, the Force of Spring1 being exerted on Rod2 was in static equilibrium with the force coming from Spring2 whose "a" point is anchored to the Fixed Point. However, at the end of this time step, this equilibrium no longer obtains, and there will be an excess force being applied to rod2 by the stretched Spring1.

STEP 3

Figure 5D:
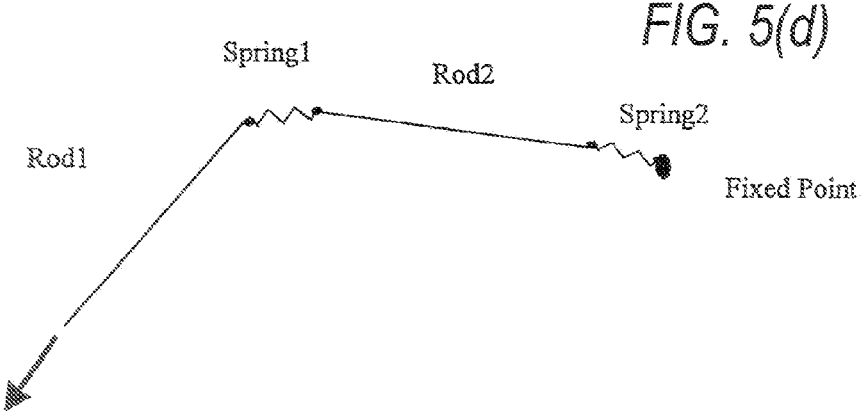

We now repeat STEP 1, but apply it to rod2 to move rod2 (see FIG. 5(d)). The applied force is the vector sum of the force generated by Spring1 and Spring2. STEP 3 may involve any number of rods or elements in the system, until all have been moved by the sum of all applied forces.

STEP 4

We return to STEP 1, and repeat it. The simulation can continue until static equilibrium is once again reached, or until another part of the software determines that it is time to stop the process.

Note:

The word "infinitesimal" in this method refers to the fact that the springs used in the simulation are mathematically designated to have a rest length of zero, and, furthermore, the spring constant k for these springs is designated to be sufficiently high, in relation to the magnitude of the applied forces and the mass and inertia of the rods, that in fact only a very small stretching of the springs occurs as the system of rods moves in response to an applied force. The authors have implemented this method in code in such a way that the visible, on the computer screen, motion of a system of two rods (representing the upper arm and forearm of the robot's arm) is such that there is no stretching of the springs. In other words, these spring joints appear to function as a joint that constrains rod1 to move in a "ball and socket" joint about the end of rod2. The amount of stretch of these zero-rest length springs with very high k constants, is literally infinitesimal.

Figure 6:
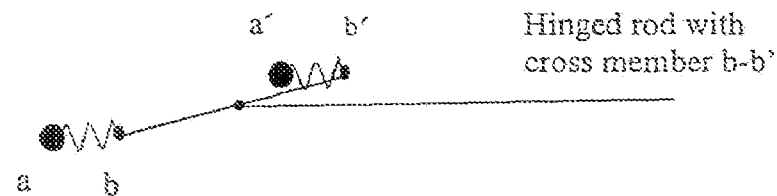
FIG. 6 illustrates obtaining hinge motion using infinitesimal spring constructs.

Discussion of Method of Obtaining Hinge Like Constrained Motion Using the Infinitesimal Spring Method In the preceding description of the method of infinitesimal springs, we saw how a ball-socket type joint was achieved. A ball-and-socket joint has two Degrees of Freedom. It is often desirable to obtain a more constrained type joint, one with just one Degree of Freedom (DoF). An example of a one DoF joint is a hinge joint. The rod-spring-rod construct as described above is not constrained to move with just one DoF. The following construct shows how to obtain a one DoF hinge joint using the method of infinitesimal springs, as follows: (Refer to FIG. 6.) What one has here are two Fixed Points a and a', to each of which is attached a spring to the b and b' particles of a cross member which is rigidly attached to the hinged rod. Because of the constraint imposed by the Fixed Points, the hinged rod can only move in a hinge like fashion. This construct has been implemented in an earlier version of the code.

Hinge Model

It is also possible to model the articulations without the use of springs, but by simply specifying equations which constrain the way that applied forces may move one rod or segment with respect to another.

Varieties of Forces that can be Used in the Physics-Based Simulation Method:

Attractive forces are applied between the end of the robot's arm and the desired target to induce the model or simulation to move in the direction of the target. Repulsive forces can be attached to an object that the robot should avoid. In essence, what we do in the model is apply a negative attractive force to induce the model to move away from an obstacle. In our prototype implementation, such an obstacle might be the position of a surgeon's hand or part of a patient's body as given by the camera-eye of the robot. This concept is capable of extension to many obstacles or to changing obstacles in response to changing conditions around the robot.

Postural or anti-gravity forces can be applied to the arm to hold it in an upright posture or whatever tilted posture is desired, since the direction of the postural force is completely up to the software. Several of these postural forces may be simultaneously applied to various parts of the robot's arm in order to cause the robot to assume and hold whatever configuration or position is desired.

4. Interaction with Surgeon:

This refers to the ability of the RST to apprehend the intentions of the surgeon, chiefly by means of verbal requests but also by means of the visual recognition of gestures, tactile inputs on various pressure-switch equipped parts of the robot such as its gripper.

Speech recognition software or hardware is a preferred embodiment of the ability of the robot to apprehend requests by the surgeon. This embodiment has been implemented by the inventors.

In terms of the robot's handing off an instrument to the surgeon, one can use some sort of tactile sensor as part of the gripper holding the instrument, such that when the robot feels the surgeon's hand coming in contact with the instrument, the robot can release the instrument to the surgeon.

Another aspect of the Interaction with Surgeon function is the use of speech synthesis technology to enable the robot to signal its understanding, or lack of understanding, of a surgeon's request. Such expressive ability can also allow the robot to query the surgeon for information that will facilitate its performance.

A preferred embodiment of the Interaction with Surgeon function is that the robot is able, in conjunction with the Cognitive System described below, to engage in fairly complicated and elaborate interactions, essentially brief conversations, with the surgeon in order to help it plan what it needs to do to anticipate and accommodate the surgeon's requests. For example, based on an internal measurement of elapsed time, the Cognitive System can prompt the robot to ask the surgeon if it is time to start closing the fascia at the end of an abdominal surgery case. Depending on the answer of the surgeon, the robot can take further actions to ready such sutures and instruments as are typically used in the closure phase of the operation.

5. Cognitive System:

Integration of the Main Functions

The essential concept of the RST is as much about the integration of these functions as it is about the specific functions or the implementation of these functions. An essential aspect of the invention of the RST is that these functions are integrated by a cognitive system that orchestrates the combined activity of these functions. This cognitive system provides the ability of the RST to function in an autonomous manner, not only functioning in a reactive mode of simply responding to the surgeon's request for an instrument, but also playing an active role in managing the surgical instruments under its care so that these instruments are ready to be handed out to the surgeon with minimal delay. The cognitive system records and remembers a particular surgeon's requests, and based on its experience with actual cases in the OR, the system will be able to anticipate these requests, further reducing the time required to get an instrument to the surgeon.

Experienced scrub technicians have situational awareness of the operation. This awareness allows the tech to track the progress of the operation as it passes from one stage to another, sensing the tempo of the operation and whether the operation is going nominally or whether there is some crisis. Situational awareness often allows tech to anticipate the next instrument the surgeon will need. Situational awareness is a higher faculty than the rote memorization of the steps of the nominal operation. The present invention teaches that, by use of a combination of existing artificial intelligence techniques, one can create a cognitive system that will enable a robot to match the situational awareness of the human scrub tech. Another key element of the present invention is the ongoing refinement of the robot's situational awareness. The robot will accomplish this by a self-reflective process using a cumulative database of actual surgeries.

Context Model

The Cognitive System of the RST consists, in a preferred embodiment, is a software system that defines the mapping from sensory input to actuator output, and thus the robot's behavior. A preferred embodiment of a Cognitive System is centered on a software object called the context model, representing the ever-changing state of the operation and the state of the robot itself. The context model is comprised of a set of assertions (statements of fact) about the overall situation, including sensor inputs, and status of the robot's output systems. All assertions are encoded in a common knowledge representation format. Various software components will be responsible for adding/taking assertions to/from the context model. These components fall into three categories: sensory, motor, and cognitive. Information will be processed within a component using whatever techniques are most appropriate. The component will then wrap the result of the processing as an assertion in the common knowledge representation format and place the assertion into the context model. This design of the present invention allows one to build components best suited to their own tasks while still integrating these components into the overall cognitive architecture.

In one embodiment, the sensor input systems comprise a machine vision system and a voice recognition system. Each sensory system corresponds to a sensor component. When something of interest to a sensor component is encountered, the sensor component will format it as a set of assertions for the context model. The vision component, for example, detects objects entering or leaving the surgical instrument drop zone. When an object is found, this component develops a representation of that perception, including instrument identification information with appropriate certainty factors. It then adds those assertions to the context model.

The output systems of the robot comprise the servomotors that move the robot's arm and the voice synthesis system. The component corresponding to an output system monitors the context model for performative assertions, those that assert that a particular action should be taken by an output system. For example, when an assertion relevant to the motor component is placed into the context model, the motor component takes that assertion from the context model, begins the motion, asserts that the motion is in progress, and finally, when the arm has reached the specified target, it asserts that the motion is complete.

Prediction Engine

Overview of Prediction Engine.

The Prediction engine is a special cognitive component. It helps the robot to anticipate the next instrument the surgeon will request, by use of machine intelligence and statistical techniques. The prediction engine takes as input a short-term memory of the recent steps of the current operation and a long-term memory of how similar operations have unfolded in the past. The prediction engine uses statistical prediction techniques as well as artificial intelligence techniques such as fuzzy logic and neural networks to predict the next likeliest request that the surgeon might make, given the immediate past history of requests during the case. This Prediction engine also draws on a database of past actual surgeries, specific to the particular surgeon doing the current case and also generalized across several surgeons. The Cognitive System is able to update and modify this data base according to the robot's experience and thereby improve the predictive performance of the robot.

Discussion of Prediction Engine

The prediction engine can use the sequence of past instrument requests to anticipate or predict the next instrument to be requested.

Background of operating room event time series. To select a prediction methodology, it is helpful to try to characterize the nature of the time series of OR instrument requests. Time series can be categorized according to the relationships between events.

1. random: The probability of the next event is not related at all to the current event but depends only on the overall probability of that event.

2. context sensitive: The next event is related to the current event and to the past N events in the time series.

3. chaotic: Events are predictable only in terms of the relationship of to a strange attractor in the phase space of system outputs.

Clinical experience in the operating room suggests that there is some type of structure or order with respect to one type of operation, repeatedly done over time, especially by the same surgeon. However, it is known by surgeons that there is always going to be some variation in the steps of an operation due to unexpected circumstances leading, sometimes, to quite unanticipated outcomes. For example, in the course of a routine operation, there may be an unexpected bleeding vessel or a vessel that requires extra dissection or extra use of electrocautery to control. It is possible, though fortunately unlikely, that due to aberrant anatomy or technical errors there may be quite unexpected consequences of these measures to control bleeding. However, it is also true that an operation can be described in at least general detail. These observations hint that perhaps the most appropriate model for the sequence of events in an operation (more precisely, in a time series of the same operation being repeated a very large number of times) is a chaotic time series. Statistical measures exist to help determine if a time series is purely stochastic versus one that has a strange attractor, which would be associated with chaotic behavior. Two measures commonly used are the correlation dimension and the correlation integral. These factors can be used to distinguish a strange attractor from a purely stochastic process.

The analysis of the nature of the instrument request time series described herein is of relevance to other areas and may prove useful for other applications aside from the robotic scrub tech. Beyond guiding our selection of a prediction engine, this analysis could be of value in other technical areas.

If operating room instrument requests are best described as a chaotic time series, the more flexible prediction methodologies, particularly neural networks and fuzzy logic, should perform better the simpler approaches. A prediction engine based on these techniques can therefore support a more comprehensive model for situational awareness that can take additional inputs from sensory systems.

Predictive models. The simplest category of predictive model relies on a flat statistical database. More sophisticated models can be constructed using Markov methods or N-sequence analysis. Finally, there are more complex prediction techniques better suited to deal with highly non-linear or chaotic time series. These techniques include neural nets and fuzzy logic After obtaining a database of surgical events from two representative small general surgical procedures, one can experimentally evaluate the predictive capability of the following methods on these data.

Stochastic or Probabilistic Models:

A flat statistical database that is essentially a histogram of the number of instrument requests versus instrument type is of interest as a baseline. The simplest approach for the robot to take in predicting the next instrument would be to always pick the one that is most commonly requested. This database is important as a benchmark for minimum performance of the more complicated methods being evaluated.

Markov Models:

The next step up in complexity is a Markov model. The first order Markov assumption is simply that the next instrument can be predicted solely the basis of the last instrument. The second order Markov model takes into account the past two instruments. This approach can be extended to higher orders but there is a price to be paid in terms of computational cost.

As an example of a first order Markov approach, Davison and Hirsh described a Unix command shell user prediction algorithm called "Incremental Probabilistic Action Modeling". Their approach is based on the Markov assumption that each command depends only on the previous command (first order Markov model). Data is collected to count the number of times each command followed each other command, thus enabling them to calculate the probability of the next future command. An interesting feature of this probabilistic model was the use of an update function with an exponential delay so that the most recent occurrence had the largest impact and later occurrences have ever-decreasing impact. This update function allowed their model to adapt to changing user patterns of command entry.

The Markov model approach is quite effective in speech recognition applications. This approach recognizes events that occur with different frequencies that are context dependent. For example, even a 1st order Markov model can generate some entertaining quasi-English utterances from a small database of actual English sentences. The 2nd order Markov model, known as a trigram model, has been used in the speech recognition community. The trigram model uses a probability distribution that is contextual only on the two most recent words in a sequence of words.

For the scrub technician scenario, our clinical experience suggests that a first order approach might be inadequate but a second order approach can have value.

N-Sequence Matching:

A related approach which can be of value is N-sequence matching. This approach has also been used in speech processing applications. A sequence of actions can be represented as a string of tokens. With prediction using sequence matching, one searches for the largest substring, up to N tokens in length, matching the current tail of the sequence. In other words, one searches for the previously encountered substring that most closely matches the current sequence. The next token is then predicted to be whichever token followed that largest matching substring. The value N defines the size of the floating window of substrings we're trying to match, thus bounding our search. Presumably, the bigger the value of N, the greater the chance that the prediction will be accurate. This approach is relevant to the clinical situation, since each instrument request can be represented by a character or other symbol and a sequence of instrument requests could correspond to a string.

Based on our knowledge of the operating room, it would appear that a more global look at the surgeon's actions may be of benefit.

Neural Nets: Feed-Forward and Recurrent:

Research has been directed, especially in recent years, to the study of neural nets for time series prediction. It has been shown that these networks are able to model real world, possibly chaotic, time series obtained from the observation of system states. Neural nets have been used to model time series generated by many types of physical phenomena including seismic data, weather data, electrical power consumption and others. Neural nets have proven particularly useful in modeling non-linear time series.

One common type of neural network configuration for time series prediction is a feed-forward net with a sliding window over past events defining the net's inputs. The inputs are the last n values of our instrument request function I(t). The output is the predicted next instrument request, denoted I(t+1).

Another important technique is the recurrent network as described by Elman. A recurrent network is defined as one in which either the network's hidden unit activations or output values are fed back into the network as inputs. These feedback connections enable Elman networks to learn to process temporal as well as spatial patterns, in effect transforming a time series into a set of contemporaneous inputs.

Implementation considerations for neural nets. There are a number of important issues to consider when designing the structure of a neural net. There is often a process of trial and error in selecting the best configuration. In particular one must consider the number of outputs, the input sequence size (the number of input nodes), the number of hidden layers, the number of nodes per hidden layer, and the learning method. The design and size of the output layer is determined by the nature of the problem. In our case it would be natural to use a 1-of-c representation, where the output is intended to classify the input stream into one of c predefined classes. In this approach we would define a set of c surgical macros (a sequence of steps that are often done together to accomplish a subtask) and the net's output would identify which of these is currently in progress. This output classification need not correspond simply to the class (the surgical macro in this case) directly, but could more generally correspond to the posterior probability of class membership. In this case, this probability assignment information can be passed into the context model of the overall cognitive architecture.

The size of the input sequence for a neural net in this situation is essentially the amount of context that is best for the predictive task. Lengthening this input sequence arbitrarily will not improve performance and may in fact degrade it. On the other hand, too small an input context will handicap the network's ability to model the underlying time series. The size of the input context can be formulated in terms of a measure called the embedding dimension, m, that arises in the functional approximation of an attractor of a chaotic time series. An approach that could be used is essentially a search based on increasing the embedding dimension, the number of inputs, until there is no further reduction in prediction error. For the present problem there is an additional heuristic that should take precedence, which is the maximum number of instrument events in a surgical macro. We believe that the largest meaningful surgical macro will be about five events.

For the number of hidden layers, it is known that an arbitrary categorization mapping or arbitrary non-linear function can be approximated by a simple multi-layer perceptron (MLP) with just an input layer, a hidden layer and an output layer. This is then be a logical place to start, adding additional hidden layers only if necessary. The number of hidden layers can also be related to the complexity or number of steps required by a domain expert (a human scrub tech in our case) to make a decision. In the present case, this should be a single step, namely recognizing from the instrument request pattern that a valid surgical macro is underway.

For the number of nodes per hidden layer, it is suggested (16) that the number of decision factors determines this number. Decision factors are the "separable elements which serve to form the unique categories of the input vector space." In our case, these would be the number of distinct instruments. This implies that we will need twelve or fewer hidden nodes.

For the learning method, the back-propagation method will be used because of its general robustness and ease of implementation.

Rule-Based Methods:

The knowledge representation of rules is very accessible to humans as opposed to knowledge encoded in the weights of a neural net. Also, the expert domain knowledge is readily available within the company. Useful rules can certainly be stated. Some of these rules are based on expert knowledge of the stages of a surgical procedure. For example, the following rules describe the closing stage.

If surgeon requests suture for fascia, then surgeon is closing

If surgeon is closing, surgeon will need suture for skin

If surgeon is closing, do final instrument count

Rules could be developed that take information from the sensory components, particularly the speech recognition system. For example, "if surgeon says 'closing', then surgeon is closing". A few "absolute" rules exist that are generally valid, regardless of the stage of the operation. For example, "If surgeon requests ties, surgeon will request suture scissors".

Fuzzy techniques could clearly make a contribution to the robot's situational awareness.

For example, consider the subtask of controlling a bleeder by placing a hemostat on the bleeder. We will call this the "control bleeder" macro. In this macro, the surgeon would call for electrocautery to coagulate a bleeding vessel after putting a hemostat on the vessel. Sometimes two hemostats might be needed, and rarely three. The "control bleeder" macro is one that would be called routinely and repeatedly as part of virtually every surgical procedure and is meant to connote the normal progress of the operation. The "control bleeder" macro might be: (hemostat, cautery) or (hemostat, hemostat, cautery) or even (hemostat, hemostat, hemostat, cautery). Fuzzy techniques could help the robot decide if a sequence of requests for hemostats is consistent with routine action of controlling normal bleeders or indicates an unusual situation. Membership functions used with the "control bleeder" macro are discussed. The variable is the number of hemostats requested in a certain time frame. This basically says that if the surgeon calls for "a few" hemostats in succession, he could well be dealing with routine bleeding as part of a routine operation. If, however, there are sequential requests for "a lot of" hemostats, something unusual is probably going on.

Reasoning System

The top-level component of the Cognitive System is a reasoning system, an inference engine that uses a set of behavioral rules to operate on the assertions contributed to the context model by the various components. The reasoning system is rule based, using an if-then declarative knowledge representation, a mainstay of current real world artificial intelligence applications. In one embodiment, one defines as much of the robot's desired behavior as possible in terms of simple logic rules, relying on more complex strategies on an as-needed basis. The reasoning system incorporates in its rules a knowledge base of the "meaning" of combinations of assertions, in terms of what the robot must do in order to best deal with the surgeon's needs. As the reasoning system processes the assertions generated by the sensor, output and prediction components, it also generates assertions that are used for final command messages to the motor and speech components. Situational awareness, as defined by what the robot does and says, arises from the integration of all of the components of its cognitive system.

As an example of how this Cognitive System works, the process of returning a discarded surgical instrument from the drop zone to the Mayo stand is described. First, the vision system detects an object in the drop zone. Second, it performs an image processing analysis, trying to match the object against the visual signatures of the known surgical instruments. Third, the vision system then asserts these results into the context model. Fourth, various rules in the cognitive control system will then be activated. Some will compare the instrument matching assertions from the vision system with current assertions about the locations of each of the instruments, trying to confirm that the tentatively identified instrument is not already known to be somewhere else. Others will consult the prediction component to determine whether that instrument is likely to be needed again soon, in which case it may be best to simply leave it on the drop zone rather than take it all the way to the Mayo stand. Fifth, after all these rules have fired, through one or more iterations, some performative assertion to the motor component is added to the context model either to return the instrument to the Mayo stand, or pick it up from the drop zone and offer it to the surgeon now, or to just let it stay out on the drop zone for the time being.

Discussion of Method Embodiment Based on Physics Based Model

Overview

An embodiment of this invention describes a method based on a physics based model of the motion of a robot arm to provide angular and positional data to specify the motion of the robot's arm so as to achieve a desired path of the robotic arm through space and toward the desired position.

This method of controlling a robotic arm is based upon physics based algorithm applied to a mathematical model of the arm being controlled.

The mathematical model of the arm is comprised of elements and junctions joining the elements. An example of an element is something with the properties of a rod. In the mathematical model, each rod is given certain basic physical properties, including total mass, length, width, height, and distribution of mass. From such basic properties, other physical properties can be derived, such as center of gravity and moments of inertia about chosen axes.

To illustrate how the physics based algorithm impacts on the mathematical model of the robot arm, we present a simple, non-limiting example of an arm comprising two elements (denoted rod1 and rod2) and two junctions (hinge type joint H1 and and hinge type joint H2). The physics based algorithm is applied to the mathematical model of the robot arm in order to generate instructions for moving the true robot arm to a target. For purpose of illustration, this example is limited to two dimensions. A three dimensional generalization of this example will be presented later in this application.

Figure 7A:
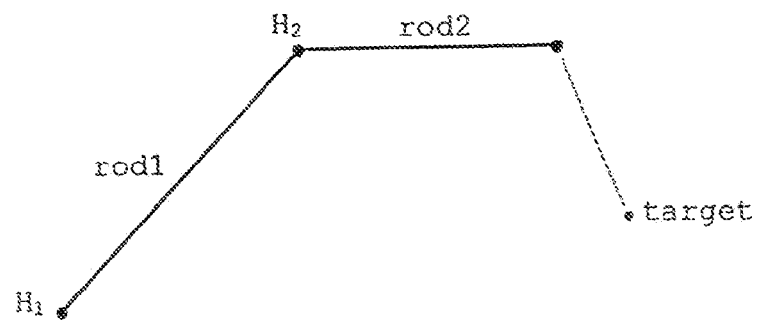
FIGS. 7(a) to 7(d) represent an example of a two-element system with two hinges: Initial position (7(a)); position after application of applied force F (7((b)); use of angular displacement alpha ($\alpha$) (7(c)); and updated position that the hinging point of Rod2 must assume (7(d))

In this two element example, as shown in FIG. 7(a), there is a hinge joint H2 between the two elements (rod1 and rod2), which permits rotation only in a plane. This type of hinge would be similar to the sort of hinge that an ordinary door moves on. There is also a hinge joint H1 at the end of rod1 and a fixed base point. Rod1 would correspond to the upper arm of the robot's arm and rod2 would be the forearm part of the arm. H2 would correspond to the elbow joint of the robot, while H1 would be a simple shoulder joint between the upper arm of the robot and its torso.

Figure 7B:
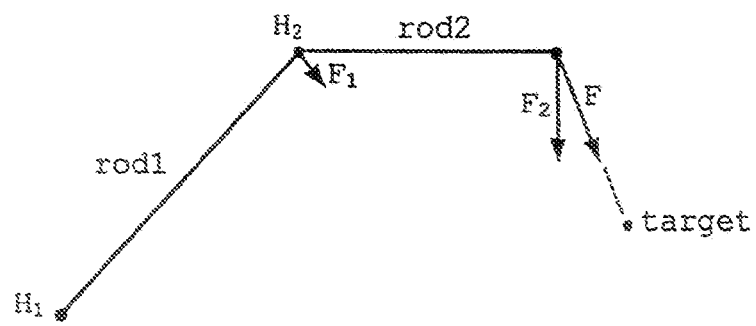

In order to get the end of rod2 to move to the target, one applies a mathematical or simulated force to the free end of rod2, directed to the target, as shown in FIG. 7(b). For that rod, one calculates the moment of the applied force about the hinge. One also calculates the moment of inertia of the rod about that hinge point. Using basic Newtonian equations of motion, one calculates, for each time step, using a method of numerical integration, such as Euler's method, the displacement of the element caused by that force.

The hinge constrains the rotation of this element to be about the axis of the hinge, in the plane perpendicular to that axis. In this example, the axis of the hinge is coming out of the plane of the two dimensional representation, and the first element is swinging on this hinge in the plane of this two dimensional representation. The constraint of the hinge is modeled in this simulation by only allowing the element connected to the hinge to respond to the component of the force that produces motion about the axis of the hinge, in the plane perpendicular to that axis. In this two dimensional example, that component of the applied force would be the force that is tangent to the circular arc that the end of rod2 describes as it swings on the hinge. If there is a component of the applied force which does not meet this constraint, that component is applied to the next rod "upstream" in the chain. In this example, that is rod1. Whether the "upstream" rod1 can be moved by that force component that is "passed through" rod2 again depends on the constraints of its respective attachment point. This process can be applied recursively to a chain of elements of any length. In this example, we have an applied force F, which is resolved into a tangenetial component F2 that is able to swing rod2 on its hinge axis, and to a component F1 which will move rod1 around its own hinge axis.

Figure 7C:
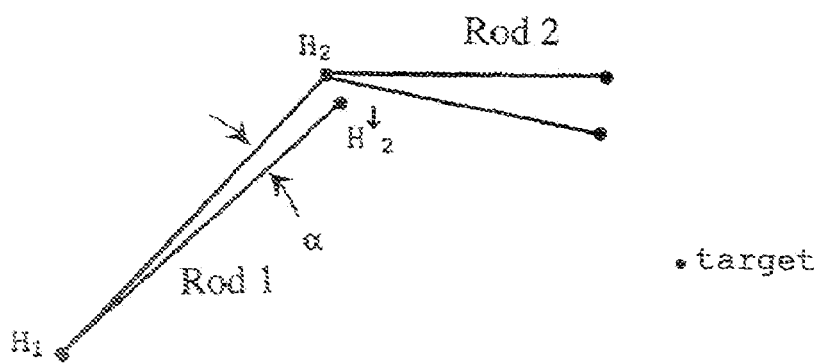

Thus, the two rods are each moved with the appropriate component of force to which their respective hinge constraint allows the rod to respond. After such an incremental move, the end of rod1 and rod2 were initially connected in the model will in general have moved apart, as shown in FIG. 7(c). In order to calculate the update of the position of rod2 to rejoin it with rod1, we use the anglular displacement of rod1. This angular displacement is calculated from the known initial and final poistion of rod1. This angular displacement must now assume to rejoin the mating hinging point of rod1. It should be understood that the amount of angular displacement and separation that the rods undergo in the simulation is numerically quite small and exists only in the simulation, not in the actual robot.

Figure 7D:
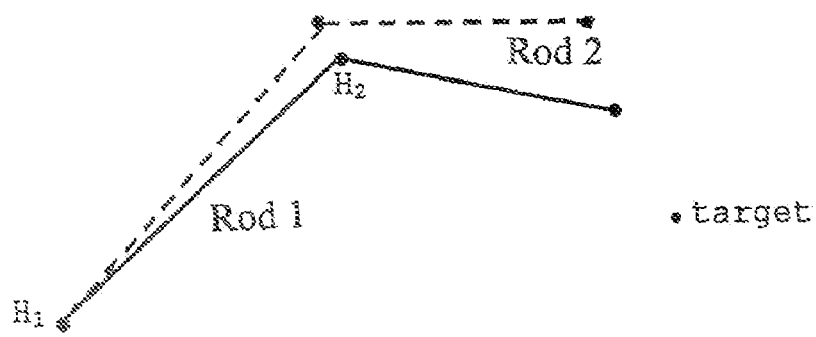

In FIG. 7(d), the rejoined rods are shown, after the two-rod system has completed an incremetal part of the move, in response to the target force. These steps are repeated until the end of rod2 has reached the target.

To control a robot, the force F is aligned so that it points to a desired target point, such as an instrument that has been located on the surgical field, and if that force was applied to the end of the rod2, which could correspond to the forearm part of a robot, then that end of the forearm will be drawn to the target. Furthermore, the use of this simulation, and the numerical integration of each incremental move, provides a mathematical description of the entire path that the end of the forearm will follow on its way to the target instrument. As the physics based simulation increments its motion to the target, other parts of the computer code measure the angle of the two hinge joints at each incremental step on the parth. These observed hinge angles are fed out to the servomotors, which actuate the robot's arm to follow to the desired target but a means (the observed simulator angles) of providing information to the robot's actuators. Thus, one can translate the mathematical description of the path to actual positional values which can be used to command servomotors. One has not only a complete description of the path in a static sense but also a time dependency for all these angles. Thus, one can provide the robot's servomotors not just with positional data but also with velocity and acceleration data. One thus has a complete method of controlling the robot.

Although the particular example was only in two dimensions, it can be extended with appropriate mathematics, to three-dimensional motion.

Standard numerical methods of integration can be employed. Application of Euler's method, and similar methods for numerical integration such as the Runge Kutta method, involve the following ideas. From Newton's second law of motion, we have Force=(mass)(acceleration)

Force=Mass$(dv/dt)$ $dv$=(Force/mass)$dt$

In other words, the incremental change in velocity can be computed by multiplying the (Force/mass) term by an incremental change in time. Therefore, we can obtain the actual velocity by means of $v=V_0+dv$, where $V_0$ is the initial velocity. Since $dx/dt=v$, we can repeat this process one more time to obtain the position coordinate x, i.e., $dx=v\,dt$. This is known as a process of numerical integration, since instead of directly integrating (twice) the second law of motion to obtain the desired v and x, we compute this approximately in finite time steps.

More Detailed Discussion

Figure 8:
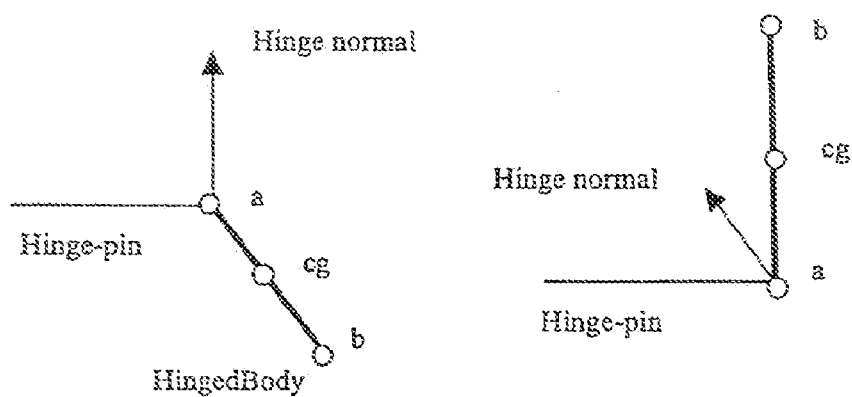
FIG. 8 represents a HingedBody rotating about its hinge-pin at the hinge-point "a"

A "HingedBody" is a type (in computer code, a subclass) of "RigidBody" whose motion is constrained to a rotation about an axis. A "RigidBody" is a mathematical construct, embodied in computer code, which models a physical rigid body, which is a physical body that has length, width, volume, mass and distribution of the mass such that there is a definite center of gravity. The axis of rotation is called the "hinge-pin". As an aid to visualization of the concepts, the HingedBody is like a door whose hinge allows the door to swing on the hinge-pin. As shown in FIG. 8, the HingedBody rotates about the pin at the point a. The "hinge normal" is a vector normal to both the hinge-pin and the body's "pointer" (a special unit vector pointing from a towards b) or the vector "aToCG" which is defined below. The HingedBody also has a center of gravity point denoted by "cg".

In the method, one constrains the body to this swinging motion by mathematically filtering the forces acting on it. Only the components of those forces along the hinge normal are allowed to act on the body (these components are applied at the force's point of application of course). The kinematics calculations then compute body position and orientation based on rotation about the hinge point a, in a vector orientation determined by the hinge-pin vector. The remainder of the forces, the components not handled by the hinge, are transferred to the "parent" RigidBody if there is one. Any transferred forces are applied to the parent's b particle. By "parent", we mean another RigidBody to which the HingedBody is attached, by a hinge joint. This parent RigidBody could be a HingedBody that in turn could be attached by a hinge to yet another RigidBody. In an embodiment of the present method, there can be a chain of HingedBodies, connected by hinges or other sorts of joints such as swivel joints. In terms of a robot arm, one models an upperarm-forearm combination by having a parent RigidBody upon which is hinged a HingedBody. This modeling can be extended to any desired number of Bodies. Other types of subclasses of the RigidBody can be defined, with different types of joints besides the hinge type discussed in detail herein. For example, there can be a PivotingBody, a SlidingJointBody, a BallSocketBody and so on.

In an embodiment wherein a parent RigidBody exists, the HingedBody is said to be attached to the parent. This gives meaning to the word "attached": the hinge point a will move along with the parent. Moreover, the orientation of the hinge pin vector will be controlled by the parent's orientation. Thus the starting position, point a, as well as the orientation of the hinge pin will be determined by the parent RigidBody. Positionally speaking, the parent RigidBody "owns" the hinge-pin and the dependent HingedBody must update its version of the hinge-pin to keep in step with the parent. It is important to note that the dynamic and kinematic calculations for the motion of HingedBody caused by the allowed forces (i.e. all forces excluding those which must be passed up to the parent as "transferForces") are independent of any motion of the parent and these calculations are all done in the body coordinate frame of the HingedBody. Motion of the parent is called "slew" motion and as described below, this slew motion will create a need for an update of the HingedBody's state variable for the hinge-pin, in order to keep the HingedBody attached to the parent's state variable for the hinge-pin. In particular the two primary kinematic state variables, momentBody and angularVelocityBody, do not include any slew motion—only hinge rotations. The quaternion and particle velocities and accelerations do, however, reflect both kinds of motion.

Initially, one calculates a useful vector, termed herein "aToCGBody", from the point "a" to the "cg" point in Body coordinates. We also calculate other useful vectors, the hinge-pin vector and the hinge normal vectors, as shown in the FIG. 8. All vectors are normalized. One uses the parallel axis theorem to compute the inertia tensor about the hinge-point, "a", given the Moment of Inertia about the center of gravity ("cg") of the HingedBody. One also initializes the orientation of the quaternion for the HingedBody and for any other RigidBody to be included in the simulation. The quaternion(s) maintain the orientation information of the Bodies and are updated as the position of the HingedBody or RigidBody changes during the successive time-steps of the simulation.

[NOTE: the "×" symbol used in the following designates the vector cross product operation.]

One can calculate the various inertia terms about the hinge point a, converting from the Moment of Inertia about the center of gravity "cg" to a Moment of Inertia about the hinge-pin at the hinge-point.

$Ixx = Icg + \text{SUM}(m_i x_i d_i))$ $Iyy = Icg + \text{SUM}(m_i y_i y_i)$ $Izz = Icg + \text{SUM}(m_i z_i z_i)$ $Ixy = Icg + \text{SUM}(m_i x_i y_i)$ $Ixz=Icg+\text{SUM}(m_i x_i z_i)$ $Iyz=Icg+\text{SUM}(m_i y_i z_i)$ where Ixx, Iyy, Izz refer to the moment of inertia terms about the three coordinate axes. In terms of the Inertia Tensor, these would be the diagonal terms. Ixy, Ixz, Iyz are the off diagonal terms, also referred to as products of inertia. The calculations are carried out according to the transfer of axis theorem. In these calculations, "$m_i$" is $i^{th}$ element of the body's total mass.

Another embodiment of the method concerns an anchor particle. An "anchor" particle is constructed coincident with the HingedBody's point "a". This anchor particle is then attached to the parent RigidBody so it will be maintained and moved with the parent. The kinematics calculations will use this particle to enforce the HingedBody's attachment, as defined above in terms of the hinge-pin, to its parent. The anchor particle, acting on the hinge point "a" and hinge-pin, enforces attachment of the HingedBody under consideration to a parent RigidBody.

Another embodiment is the use of a transfer force. A specially useful force, the "transferForce" can also be calculated here. This force is used to pass the unconsumed remainder forces on to the parent RigidBody of this Hinged-Body. If the parent has a particle called "transferForceAttachPoint", the force will be applied there. Otherwise it will be applied to the parent's "b" particle. Visually, this makes sense if we think a two rod robotic arm, with the forearm rod's "a" point attached to the "b" point of the upperarm rod.

One can do the dynamics calculation of the effect of the applied forces on the HingedBody. One performs this dynamics calculation for each time-step of the simulator. The following equations describe these calculations. These calculations are done in body coordinates in order to take advantage of the invariance of the Moment of Inertia in this coordinate system. These calculations also make use of a quaternion representation of the orientation of the Hinged-Body and parent RigidBody (if there is a parent). The reason for using quaternions is that a quaternion is easily, and singularity freely, updated by an angular velocity to a quaternion with an new orientation.

I. Summary of Principal Steps per Time-Step of Simulation Method

STEP 1: CALCULATING TOTAL MOMENT OF FORCES $Mh=\text{SUM}(Ri \times (Fb \text{ dot } Nb)Nb)$

STEP 2: UPDATING ANGULAR VELOCITY $w=w+dt Ih^{-1}(Mh-(w \times Ihw))$

STEP 3: UPDATING QUATERNION OF HINGEDBODY WITH MOTION ABOUT HINGE $q=q+dt/2 wq$

STEP 4: UPDATING QUATERNION AGAIN WITH SLEW MOTION OF PARENT $q=q+dt/2 w'q$ aToCGBody+anchor

STEP 5: FINDING ANGLE OF HINGEDBODY FOR OUTPUTTING TO SERVOMOTORS

Calculate angle theta for the HingedBody relative to starting angle
Where . . .
Mh total Moment of Force about hinge point h in Body coordinates
Nb hinge normal vector in Body coordinates
Ri moment arm of application of force Fi in Body coordinates
$Fb=\sim q(Fi)q$, which is the Fi rotated from World into Body coordinates
Ih Moment of Inertia about h in Body coordinates
$Ih^{-1}$ Inverse of Moment of Inertia
w angular velocity about h in Body coordinates
q quaternion for orientation of the HingedBody
dt delta t, the time-step for the simulation
theta angular position of HingedBody about hinge-pin There are embodiments employing different coordinate systems. A note of explanation about the coordinate systems used in this example now follows: There are two coordinate systems in which we do our calculations. These are World coordinates, which is a fixed and universal coordinate system in which the various RigidBodies may move. Ultimately this is the coordinate system in which the robot moves. There is also a Body coordinate system an instance of which exists for each and every RigidBody. It is convenient mathematically, as described below, to do calculations pertaining to rotational motion of the RigidBody in the Body coordinate system. However, the various Forces that may be applied as target forces to the RigidBodies and HingedBodies making up the system are applied from the perspective of World coordinates, and also the motion of the robot arm ultimately is ultimately viewed in terms of World coordinates. One is able to mathematically convert back and forth between these coordinate systems as required.

Consider the principal steps of this method:

STEP 1: Calculating Total Moment of Forces

At this stage of the calculation, one checks to see if one has to deal with any transfer forces which were passed from a RigidBody to which our HingedBody is a parent. These "transferForces" are defined to represent components of force that were not allowed to be handled under the constraints of the joint between the HingedBody we are considering and some other RigidBody further "downstream" in the kinematic chain (i.e. a RigidBody to which our Hinged-Body is the "parent"). If we do have such transferForces, they are added to the collection of forces Fi that are handled in EQUATION 1.

The first thing one needs to do is to convert the applied Forces, Fi, from World coordinates to Body coordinates, which is coordinate system attached to the HingedBody itself. One makes use of the quaternion q, which describes the orientation of HingedBody, to effect this transformation.

$Fb=\sim q(Fi)q$ where ~q is the conjugate of the quaternion q. This equation in effect rotates the Fi vector from World coordinates into the Body coordinate system. One chooses to do these calculations in the Body coordinate system to have an invariant Moment of Inertia.

The quaternion q is of course the quaternion from the previous time-step of the simulation.

In the following calculations, one constrains the forces acting on the HingedBody to only those components in the direction the hinge-normal. The remainder of the force is passed on as part of the transferForce where they might be handled by the parent RigidBody. This is mathematically how the construct of a hinge is achieved.

Now, this calculation is:

$Mh=\text{SUM}(Ri \times (Fb \text{ dot } Nb)Nb)$ where Mh is the Moment of Force about the hinge-pin and where Nb is the hinge-normal vector. The component of applied force that we allow to move the HingedBody is given by the dot product of the Force (in Body coordinates) and the Hinge-normal, also in Body coordinates. In other words, as in the two dimensional example shown above, only the component of applied force which is instantaneously tangential to the arc of motion that the HingedBody describes is allowed to act on the HingedBody. The hinge-normal vector serves the purpose of "filtering" the applied forces to obtain only those components that satisfy the hinge constraint.

With the just obtained Moment of Forces Mh, one can evaluate the change in angular velocity over our time-step t, using the inverse of the Moment of Inertia $Ih^{-1}$, again all in Body coordinates. The main reason for doing rotational calculations in Body coordinates lies in this step. As long as we stay in Body coordinates, the Moment of Inertia Ih will be the same and so we only need to calculate its inverse once. If we were to do the this calculation in World coordinates, we would have to re-evaluate Ih and its inverse at every time step of the simulation, which is computationally expensive. We save on computations this way even if we have to first convert the applied forces Fi from world to body coordinates using the quaternion and its conjugate and the dot product of the hinge-normal.

STEP 2: Updating Angular Velocity

In this step, one now actually uses Euler's method, a simple type of numerical integration, to get an approximation of the angular velocity, by adding an update term at to the angular velocity w from the previous time-step. Again, note that "dt" in these equations a small interval of time, corresponding to one "tick" or time-step of the simulation.

Here is EQUATION 2, in which one updates, using Euler's method, the angular velocity:

$$w=w+dt Ih^{-1}(Mh-(w \times Ihw))$$

Note:

There appears to be an "extra" term in this equation $w \times (Ihw)$.

This term arise from the general equation of motion in a frame that is rotating with angular velocity w respect to a fixed frame $$Mh=Ih(dw/dt)+w \times (Ihw)$$

STEP 3: Updating Quaternion of HingedBody with Motion about Hinge

Next, one updates the quaternion describing the orientation of the HingedBody by means of the following equation, sometimes referred to as Poinsot's equation:

$$q=q+dt/2wq$$

This equation shows how to effect an update of the quaternion when the quaternion is rotated at an angular velocity w. In this expression, the value of q on the left hand side of the equation is the value of q at the current time step, and it is computed by adding, on the right hand side of the equation, the value of q from the previous time step and the term dt/2wq which represents the change in q resulting from the angular velocity applied over the time-step dt. This elegant expression is the reason why one prefers to handle the rotational calculations using quaternions instead of rotational matrices, which can also be used.

This takes care of updating the HingedBody's quaternion in terms of the new angular velocity of the motion of the HingedBody expressed in the body coordinate frame.

STEP 4: Updating Quaternion Again with Slew Motion of Parent

Now, one updates the quaternion once more, by means of a calculation of the angular velocity w' which corresponds to the amount of motion of the parent RigidBody to which the HingedBody is attached.

$$q=q+dt/2w'q$$

This angular velocity w', referred to as the "slew" angular velocity, is found by calculating the angular displacement between the current orientation of the hinge-pin as seen by the parent RigidBody and a reference hinge-pin vector as seen by the HingedBody, (this reference hinge-pin vector was calculated and saved from the previous time-step of the simulation), and then dividing that angular displacement by the length of time in the time-step. Obviously, if the parent's state variable for the hinge-pin has moved away from the state variable of the hinge-pin that our HingedBody "remembers", then there will be need to do an update of the HingedBody's version of the hinge-pin.

To actually calculate the hinge-pin's orientation according to the parent, one rotates the hinge-pin as seen by the HingedBody (i.e. using the hinge-pin state variable belonging to the HingedBody) into World coordinates using the quaternion of the parent RigidBody.

Another part of this update of the quaternion of the HingedBody is to update the aToCGbody vector with the new anchor vector, reflecting the change in the position of the parent RigidBody. One does this as follows, by means of the previously defined "anchor" point which is part of the parent Body.

aToCGBody+anchor recalculate cg of HingedBody

This update in effect moves the starting point of the aToCG vector in World coordinates, so that the actual position of HingedBody (as denoted by its central cg point) is also appropriately updated to reflect motion of the parent Body in the World coordinate system.

After this update, one saves a reference copy of the changed hinge-pin vector, that will be used to calculate the slew angular displacement in the next time-step of our simulation.

STEP 5: Finding Angle of HingedBody for Outputting to Servomotors

The final step is to calculate the angle at which our HingeBody is pointing, relative to an initial angle reference specified at the start of the simulation. As described earlier, this angle can be transmitted out to the give directional control to the servos moving the actual physical robot. This transmission in one embodiment is done by means of a USB port which communicates with a microcontroller, programmed in appropriate assembly language, which converts these numerical angular values to a form of pulse width encoded position data which can be interpreted by the servomotor hardware to assume the required rotational position.

This step is how the simulation is used to communicate with the physical servos and thus command the robot's members to move.

The main equation here is another application of Euler's method, to the angular position variable of the HingedBody:

$$theta=theta+dt(w \text{ dot hinge-pin}).$$

Where as before dt is the time-step of the simulation. Taking the dot product of the angular velocity w with the hinge-pin insures that we are only considering component of the angular velocity in the appropriate plane to preserve the constraint of hinge motion. As has been done before, the left hand side of the equation represents the value of theta at the current time step, while the right hand of the equation is the sum of the value of theta from the previous time step plus the term representing the update from the (appropriate component of) angular velocity multiplied by the time-step value dt.

A Preferred Embodiment of the Overall Robot

Figure 2:
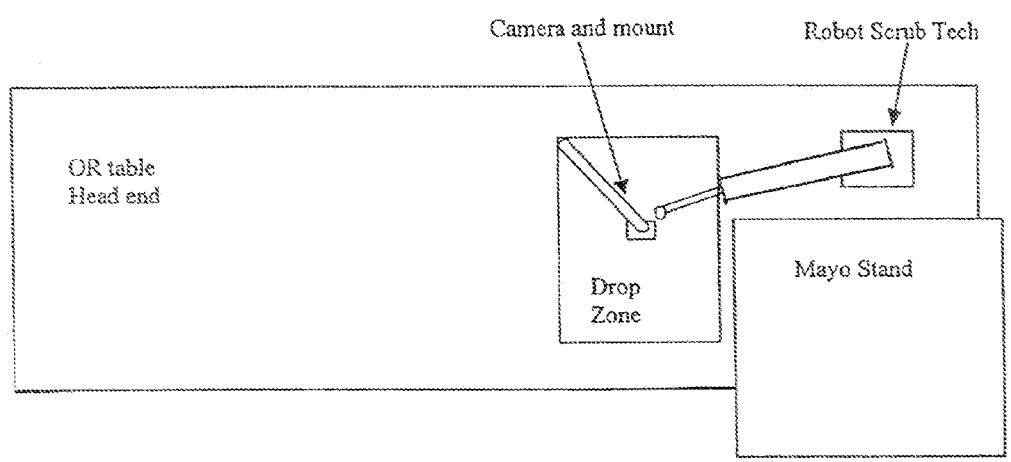
FIG. 2 is a top view of a layout of an embodiment of the invention such as shown in FIG. 1.
Figure 3:
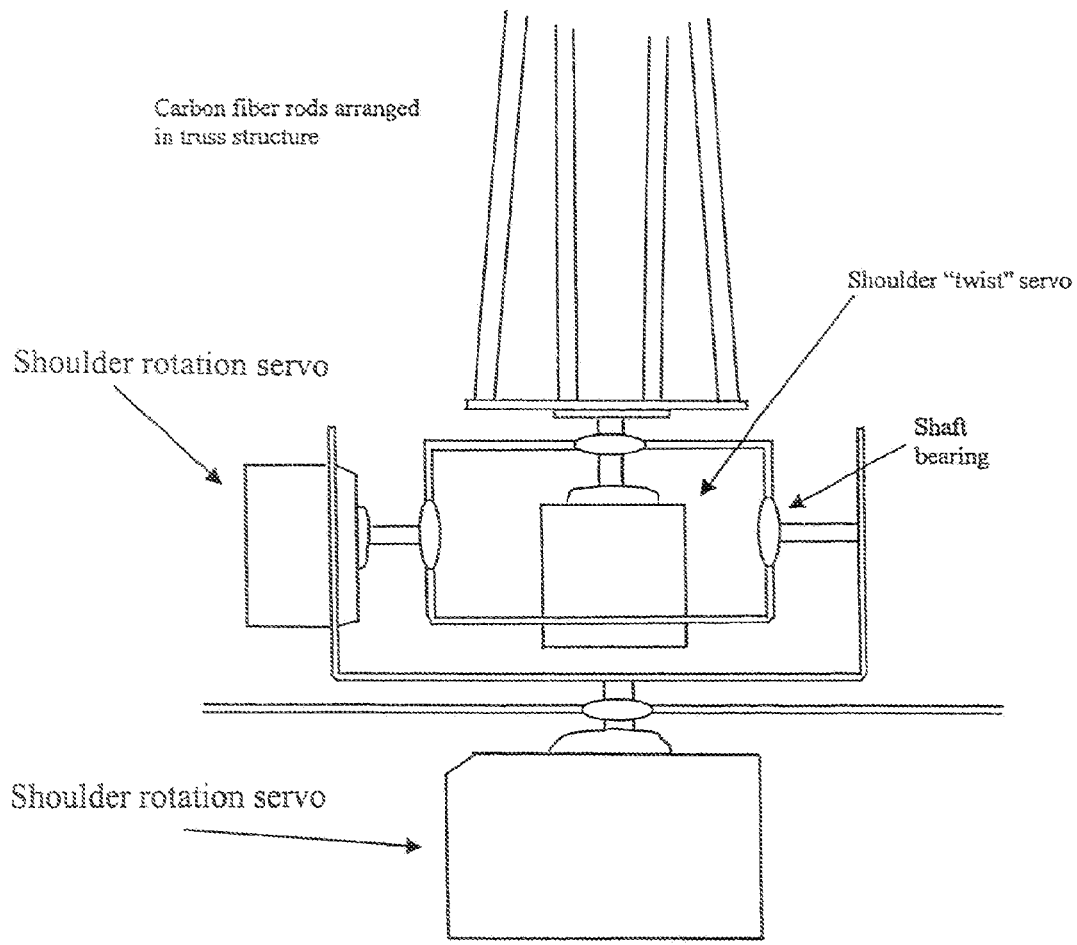
FIG. 3 represents a detail of an embodiment of the invention such as shown in FIGS. 1 and 2, showing the "twist" degree of freedom with the arm pointing straight up. Carbon fiber rods form a very light and stiff structure.

One preferred embodiment of the overall mechanical design of the robot is indicated in FIG. 1, a schematic of an actual working prototype. This prototype has an arm with an elbow joint, and a shoulder (FIG. 3). The elbow has one degree of freedom and is able to bend, with the same range of motion as a human elbow joint. The shoulder has three degrees of freedom that are rotation about a horizontal axis which is parallel to the axis of the elbow, rotation about a vertical axis and rotation about an axis which runs through the center of the upper arm. These motions are comparable to the range of motion of a human shoulder. The arm is also fitted with a gripping device to pick up and hold surgical instruments. In the prototype shown, a electromagnetic gripping device is used (FIG. 4). As shown in FIGS. 1 and 2, the robot is equipped with a digital camera that is mounted on a boom that overlooks the operating field. This camera is connected to the central control computer and provides input to the software that recognizes and locates instruments. This embodiment can perform all of the following functions:

1. Recognize surgeon's request
2. Select correct instrument from Mayo stand
3. Hand the instrument to surgeon
4. Wait for surgeon to lay instrument on drop zone
5. Visually locate instrument
6. Identify instrument
7. Return instrument to Mayo stand in proper orientation Embodiments of the present invention include a device, which can perform one or more of the steps of recognizing a request from a human for an object, selecting the correct object in response to the request, handing the object to a human, waiting for the human to finish with the object and to lay the object down, locating the laid down object, identifying the laid down object, and returning the object to its proper location. Embodiments of the present invention include a method for the movement of an object comprising one or more of the following steps: recognizing a request from a human for an object, selecting the correct object in response to the request, handing the object to a human, waiting for the human to finish with the object and to lay the object down, locating the laid down object, identifying the laid down object, and returning the object to its proper location, wherein each step is performed by a robotic device.

Other Embodiments

Besides the prototype described above, there are other embodiments that may be useful. Instead of an articulated arm to dispense the instruments to the surgeon from the instrument tray, it may for some applications be desirable to have another means for dispensing the instruments. For example, a rotary tray with slots to hold each instrument might be used. Another might be a conveyor belt type system. Another might be a system which uses a vibrating channel or conduit to move instruments from a cache area to a pick up point for the surgeon to take up the instrument.

A further class of embodiments would be the combination of the above functions with a mobile base of some sort, perhaps a mobile platform that was on wheels. Such a mobile unit could be used to dispense and retrieve other items using machine vision and speech recognition technologies as major input modes. Such a device might function in work environments other than the operating room. One embodiment would be a mobile robot that could perform some of the more mundane functions of an airline stewardess (handing out peanuts, checking to see if belts are buckled, collecting trash).

The present invention has still other embodiments:

1. There is an embodiment for a device for manipulating a surgical instrument in an operating room which device possesses speech recognition capabilities such that it associates a specific spoken word or words with a specific surgical instrument, which possesses machine vision capabilities to identify that specific surgical instrument, and which device is capable of picking up that specific surgical instrument in response to the spoken word or words.

2. There is an embodiment for a device for manipulating a surgical instrument in an operating room which device possesses speech recognition capabilities such that the device recognizes a request to give a surgical instrument to a human, possesses machine vision capabilities to recognize the identity of the surgical instrument, and possesses the capability to return the surgical instrument to its appropriate place on the Mayo stand.

3. There is an embodiment for a device for manipulating a surgical instrument in an operating room which device possesses artificial intelligence capabilities to recognize the need to give a surgical instrument to a human, possesses machine vision capabilities to recognize the identity of the surgical instrument, and possesses the capability to return the surgical instrument to its appropriate place on the Mayo stand.

4. There is an embodiment for a device for manipulating a surgical instrument in an operating room which device is capable of picking up a specific surgical instrument in response to a spoken word or words and which moves the instrument according to a physics based algorithm described in the present application.

5. There is an embodiment for a device for manipulating a surgical instrument in an operating room which device is capable of picking up a specific surgical instrument in response to a spoken word or words and which picks up the surgical instrument at, or approximately at, its two-dimensional center-of-mass, as calculated by the device using machine vision.

6. There is an embodiment for a device for manipulating an object which device is capable of picking up a specific object in response to a spoken word or words and which picks up the object at, or approximately at, its two-dimensional center-of-mass, as calculated by the device using machine vision.

7. There is an embodiment for a device for manipulating an object which device is capable of picking up a specific object in response to a spoken word or words, which picks up the object at, or approximately at, its two-dimensional center-of-mass, as calculated by the device using machine vision, and which moves the object according to a physics based algorithm described in the present application.

The physics-based algorithm has other embodiments. There is a method for moving an arm of a robot comprising the steps of modeling the arm of the robot to create a model comprising elements of finite mass joined by junctions, which junctions may comprise springs or hinges; using an algorithm to determine results of the effect of applying force to the elements of the model; and using the results to define a path for the arm of the robot.

This method may include one or more of the following steps:

using the mathematical construct of an infinitesimally long spring with a high spring constant to model joints of robot arm. Infinitesimal springs means springs of zero rest length whose working length under application of typical forces is extremely (infinitesimally) small such that the model whose joints are composed of such springs does not appear to move in a stretching manner when observed on a normal computer screen;

using the mathematical construct of an infinitesimally long spring to model a ball-and socket joint with two degrees of freedom;

using rigid body elements with mass, center of gravity, distribution of mass, moments of inertia as part of the physics based simulation;

using rigid body elements to which may be attached cross members of particles rigidly affixed to the rigid body, in order to provide attachment at the cross members for additional infinitesimal springs;

using combinations of such infinitesimally long springs to model joints with one degree of freedom, which is less than could be done by any single spring joint;

using the mathematical construct of Fixed Points in space to anchor the infinitesimal springs in order to produce desired constraints on the motion of the physics based simulation;

using mathematical filtering of the applied forces on a joint to constrain a joint to move in a desired way;

using "transfer forces" which will be passed from one rigid body element of a chain of elements in order to produce motion of succeeding elements of that chain;

using attractive forces to induce the physics based simulation of the robot arm to approach a desired target;

using repulsive forces to induce the physics based simulation of the robot arm to avoid certain locations in the path of the robot;

using postural forces to induce the physics based simulation to maintain an upright attitude, or to assume any other attitude such as leaning sideways or drooping;

using such postural forces to modify the attitude of the robot arm as it approaches a target, so that it may approach in less obtrusive way relative to the surgeon;

running the physics based simulation in an incremental, time-stepping manner which allows for additional computer code to incrementally observe the angular position of the physics based simulation and to incrementally update the position of real servomotors comprising the robot; and simulating a joint between two RigidBodies by mathematically linking the quaternions describing the orientation of a child and parent in a model, such that the quaternion of child is update by the quaternion of the parent, after each time-step of the simulation, in order to ensure continued linkage of the parent and child as in a real joint.

Figure 9:
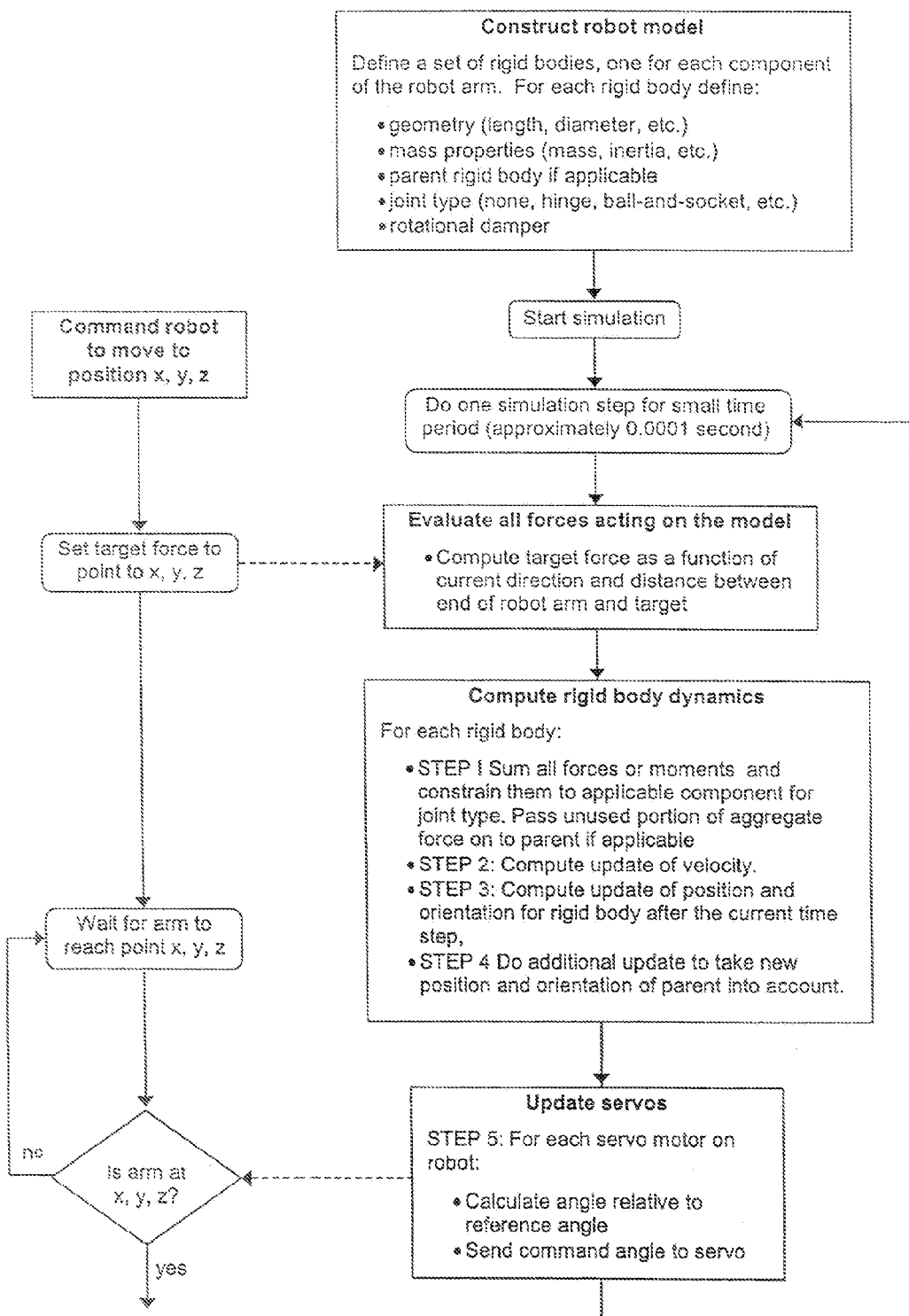
FIG. 9 is a flowchart that interrelates robot command and control with physics simulation.

An embodiment of the invention is presented in a flowchart interrelating robot command and control and the physics simulation (see FIG. 9).

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. A method for manipulating a surgical instrument or product in an operating room by a robotic system, comprising:
    initiating a search for the instrument or product;
    autonomously identifying the instrument or product by a characteristic feature;
    autonomously determining the location of the instrument or product;
    autonomously picking up the instrument or product;
    autonomously moving the instrument or product from a first location to a second location; and
    autonomously releasing the instrument or product,
    wherein each step is performed by the robotic system and the robotic system is capable of selecting an instrument or product, presenting the instrument or product to a surgeon, and retrieving the instrument or product after use.

2. The method of claim 1, wherein the search is initiated by the robotic system in response to a human command.

3. The method of claim 2, wherein the search is initiated in response to a human command made by voice and received by a voice recognition system.

4. The method of claim 1, wherein the search is initiated by artificial intelligence.

5. The method of claim 1, wherein the search is initiated autonomously by the robot.

6. The method of claim 1, wherein the surgical instrument or product is identified by size.

7. The method of claim 1, wherein the surgical instrument or product is identified by color.

8. The method of claim 1, wherein the surgical instrument or product is identified by aspect ratio.

9. The method of claim 1, wherein the surgical instrument or product is identified by bar coding.

10. The method of claim 1, wherein the surgical instrument or product is picked up by use of an electromagnet.

11. The method of claim 10, wherein the surgical instrument or product is picked up by an electromagnet that can be controlled by the robotic system to turn off at the appropriate time to release the surgical instrument or product to a surgeon.

12. The method of claim 1, wherein the surgical instrument or product is picked up by use of suction.

13. A robotic system for manipulating a surgical instrument or product in an operating room which is capable of responding to a request for a surgical instrument or product, autonomously identifying a surgical instrument or product by use of machine vision, autonomously picking up the surgical instrument or product, autonomously moving the surgical instrument or product, and autonomously releasing the surgical instrument or product, wherein the robotic system is capable of selecting an instrument or product, presenting the instrument or product to a surgeon, and retrieving the instrument or product after use.

14. The system of claim 13, wherein the request is made by sound.

15. The system of claim 13, wherein the request is made by a human being.

16. The system of claim 13, wherein the request is made by artificial intelligence.

17. The system of claim 13, wherein the surgical instrument is identified by size.

18. The system of claim 13, wherein the surgical instrument or product is identified by color.

19. The system of claim 13, wherein the surgical instrument or product is picked up by means of magnetic forces.

20. The system of claim 13, wherein the surgical instrument or product is picked up by means of a magnet applied to the center of mass of the surgical instrument or product.

21. The system of claim 13, wherein the request is made by the voice of a human being and the surgical instrument or product is identified by color.

22. The system of claim 13, wherein the request is made by the voice of a human being and the surgical instrument or product is picked up by means of magnetic forces.

23. The system of claim 13, wherein the request is by artificial intelligence and the surgical instrument or product is picked up by means of magnetic forces.

24. A robotic system comprising an arm for manipulating a specified object, which system is capable of autonomously picking up the object in response to a spoken word or words and which picks up the object utilizing the arm, wherein the arm moves by means of instructions created by an algorithm wherein calculations are made based upon the analysis of application of attractive, repulsive, and postural theoretical forces to components of a model, said components comprising elements of finite mass joined by junctions, wherein the robotic system is capable of selecting an instrument or product, presenting the instrument or product to a surgeon, and retrieving the instrument or product after use.

25. The system of claim 24, wherein the specified object is picked up at, or approximately at, its two-dimensional center-of-mass, as calculated by the device using machine vision.

26. A method for manipulating a surgical instrument or product in an operating room by a robotic system, comprising the steps of:
   autonomously initiating a search for the instrument or product;
   autonomously identifying the instrument or product by a characteristic feature;
   autonomously determining the location of the instrument or product;
   autonomously picking up the instrument or product;
   autonomously moving the instrument or product from a first location to a second location; and
   autonomously releasing the instrument or product,
   wherein each step is performed by the robotic system and the robotic system is capable of selecting an instrument or product, presenting the instrument or product to a surgeon, and retrieving the instrument or product after use.

27. The method of claim 26, wherein the search is initiated by the robotic system in response to a human command.

28. The method of claim 27, wherein the search is initiated in response to a human command made by voice and received by a voice recognition system.

29. The method of claim 26, wherein the surgical instrument or product is identified by size, color, aspect ratio, or bar coding.

30. The method of claim 26, wherein the surgical instrument or product is picked up by use of an electromagnet or suction.

31. A robotic system for manipulating a surgical instrument or product in an operating room which is capable of responding to a request for a surgical instrument or product, identifying the surgical instrument or product by use of machine vision, picking up the surgical instrument or product, moving the surgical instrument or product, and releasing the surgical instrument or product, wherein the robotic system is capable of selecting an instrument or product, presenting the instrument or product to a surgeon, and retrieving the instrument or product after use.

32. The system of claim 31, wherein the request is made by sound or artificial intelligence.

33. The system of claim 31, wherein the surgical instrument or product is identified by size, color, aspect ratio, or bar coding.

34. The system of claim 31, wherein the surgical instrument or product is picked up by means of magnetic forces or suction.

* * * * *